(12) United States Patent
Hawes et al.

(10) Patent No.: US 12,377,231 B2
(45) Date of Patent: *Aug. 5, 2025

(54) POD ASSEMBLY, DISPENSING BODY, AND E-VAPOR APPARATUS INCLUDING THE SAME

(71) Applicant: Altria Client Services LLC, Richmond, VA (US)

(72) Inventors: Eric Hawes, Midlothian, VA (US); Raymond Lau, Richmond, VA (US); Alistair Bramley, Richmond, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 389 days.

This patent is subject to a terminal disclaimer.

(21) Appl. No.: 17/835,272

(22) Filed: Jun. 8, 2022

(65) Prior Publication Data
US 2022/0354171 A1  Nov. 10, 2022

Related U.S. Application Data

(63) Continuation of application No. 16/441,086, filed on Jun. 14, 2019, now Pat. No. 11,357,934, which is a (Continued)

(51) Int. Cl.
*A61M 15/00* (2006.01)
*A24F 40/40* (2020.01)
(Continued)

(52) U.S. Cl.
CPC ......... *A61M 15/0065* (2013.01); *A24F 40/40* (2020.01); *A24F 40/42* (2020.01);
(Continued)

(58) Field of Classification Search
CPC .................. A61M 15/0065; A61M 15/06; A61M 11/042; A61M 40/53; A61M 40/40;
(Continued)

(56) References Cited

U.S. PATENT DOCUMENTS

D112,702 S   12/1938  Kirsten
D127,009 S   5/1941   Gebhart et al.
(Continued)

FOREIGN PATENT DOCUMENTS

CN   1575673 A    2/2005
CN   302311408    1/2013
(Continued)

OTHER PUBLICATIONS

Office Action dated Dec. 22, 2023 issued in related Malaysian patent application No. PI2020004926.
(Continued)

*Primary Examiner* — Harshad C Patel
(74) *Attorney, Agent, or Firm* — Harness, Dickey & Pierce, P.L.C.

(57) ABSTRACT

At least one example embodiment discloses a pod for an electronic vapor (e-vapor) apparatus. The pod includes a pre-vapor formulation compartment configured to hold a pre-vapor formulation therein, a device compartment in fluidic communication with the pre-vapor formulation compartment, the device compartment including a processor configured to monitor the pre-vapor formulation compartment and identify the pre-vapor formulation and a vapor channel extending from the device compartment and through the pre-vapor formulation compartment.

12 Claims, 16 Drawing Sheets

Related U.S. Application Data continuation of application No. 15/135,932, filed on Apr. 22, 2016, now Pat. No. 10,327,474.

(60) Provisional application No. 62/151,160, filed on Apr. 22, 2015, provisional application No. 62/151,179, filed on Apr. 22, 2015.

(51) Int. Cl.
| | |
|---|---|
| *A24F 40/42* | (2020.01) |
| *A24F 40/53* | (2020.01) |
| *A61M 11/04* | (2006.01) |
| *A61M 15/06* | (2006.01) |
| *A24F 40/10* | (2020.01) |

(52) U.S. Cl.
CPC ........... *A24F 40/53* (2020.01); *A61M 11/042* (2014.02); *A61M 15/06* (2013.01); *A24F 40/10* (2020.01); *A61M 2205/276* (2013.01); *A61M 2205/3334* (2013.01); *A61M 2205/60* (2013.01)

(58) Field of Classification Search
CPC .................. A61M 40/42; A61M 40/10; A61M 2205/276; A61M 2205/3334; A61M 2205/60
USPC .......................................................... 131/329
See application file for complete search history.

(56) References Cited

U.S. PATENT DOCUMENTS

| | | |
|---|---|---|
| D176,226 S | 11/1955 | Gebhart et al. |
| D217,841 S | 6/1970 | Bulger et al. |
| 3,986,516 A | 10/1976 | Brooks |
| 3,998,232 A | 12/1976 | Smith |
| 4,686,353 A | 8/1987 | Spector |
| D292,324 S | 10/1987 | Decker et al. |
| D301,618 S | 6/1989 | Barros |
| 4,947,874 A | 8/1990 | Brooks et al. |
| D317,407 S | 6/1991 | Gray et al. |
| D367,608 S | 3/1996 | Stranders |
| D368,552 S | 4/1996 | Adams |
| D373,536 S | 9/1996 | Kokenge et al. |
| 5,666,977 A | 9/1997 | Higgins et al. |
| D401,507 S | 11/1998 | Gonda et al. |
| D422,113 S | 3/2000 | Higgins et al. |
| D424,236 S | 5/2000 | Reed |
| D424,739 S | 5/2000 | Ross |
| D433,532 S | 11/2000 | Higgins et al. |
| D433,744 S | 11/2000 | Basaganas |
| D438,459 S | 3/2001 | Holthaus |
| D446,499 S | 8/2001 | Andre et al. |
| D484,806 S | 1/2004 | Cummings |
| D522,272 S | 6/2006 | Vanhee |
| D527,640 S | 9/2006 | Cummings et al. |
| D532,927 S | 11/2006 | Sann |
| D532,972 S | 12/2006 | Dixon |
| D544,956 S | 6/2007 | Collins et al. |
| D546,940 S | 7/2007 | Collins et al. |
| D547,440 S | 7/2007 | Louet-Feisser |
| D547,859 S | 7/2007 | Choi |
| D552,230 S | 10/2007 | Collins et al. |
| D552,232 S | 10/2007 | Collins et al. |
| D552,730 S | 10/2007 | Collins et al. |
| D562,761 S | 2/2008 | Ueda et al. |
| D569,794 S | 5/2008 | Zhang et al. |
| D577,150 S | 9/2008 | Bryman et al. |
| D579,544 S | 10/2008 | Birath et al. |
| D579,545 S | 10/2008 | Birath et al. |
| D579,547 S | 10/2008 | Birath et al. |
| D579,549 S | 10/2008 | Birath et al. |
| D588,741 S | 3/2009 | Murdaugh, III et al. |
| 7,699,052 B2 | 4/2010 | Schiewe et al. |
| 7,753,055 B2 | 7/2010 | Bryman |
| D623,129 S | 9/2010 | Kawakami et al. |
| D629,154 S | 12/2010 | Sung |
| D643,807 S | 8/2011 | Jiang |
| D649,708 S | 11/2011 | Oneil |
| D650,520 S | 12/2011 | Timmermans |
| D650,737 S | 12/2011 | Hamilton |
| D654,160 S | 2/2012 | Yomtov |
| 8,205,622 B2 | 6/2012 | Pan |
| D663,686 S | 7/2012 | Yang |
| D664,920 S | 8/2012 | Huang |
| D665,346 S | 8/2012 | Kumagai et al. |
| D665,734 S | 8/2012 | Fitch et al. |
| D672,714 S | 12/2012 | Brandys et al. |
| D682,197 S | 5/2013 | Leung |
| D683,626 S | 6/2013 | Beck et al. |
| D686,153 S | 7/2013 | Qu |
| D689,818 S | 9/2013 | Sasada |
| 8,528,569 B1 | 9/2013 | Newton |
| 8,550,069 B2 | 10/2013 | Alelov |
| D693,053 S | 11/2013 | Chen |
| D694,468 S | 11/2013 | Chen |
| 8,689,804 B2 | 4/2014 | Fernando et al. |
| 8,707,965 B2 | 4/2014 | Newton |
| D705,719 S | 5/2014 | Wong |
| 8,820,330 B2 | 9/2014 | Bellinger et al. |
| D718,492 S | 11/2014 | Albanese |
| D720,094 S | 12/2014 | Alima |
| D720,497 S | 12/2014 | Alima |
| D720,884 S | 1/2015 | Liu |
| D723,215 S | 2/2015 | Chen |
| D723,216 S | 2/2015 | Chen |
| 8,955,522 B1 | 2/2015 | Bowen et al. |
| D725,310 S | 3/2015 | Eksouzian |
| D725,588 S | 3/2015 | Iaconis et al. |
| 8,977,115 B2 | 3/2015 | Penman, Jr. |
| D727,566 S | 4/2015 | Xiao |
| D728,855 S | 5/2015 | Liu |
| D729,444 S | 5/2015 | Leidel |
| D729,445 S | 5/2015 | Leidel |
| D730,282 S | 5/2015 | Miller et al. |
| D730,572 S | 5/2015 | Leidel |
| D731,114 S | 6/2015 | Leidel |
| D733,050 S | 6/2015 | Chiang |
| D733,744 S | 7/2015 | Capela et al. |
| 9,072,321 B2 | 7/2015 | Liu |
| D736,090 S | 8/2015 | Kikuchi |
| 9,095,175 B2 | 8/2015 | Terry et al. |
| D738,038 S | 9/2015 | Smith |
| D743,099 S | 11/2015 | Oglesby |
| D748,325 S | 1/2016 | Leidel |
| D750,321 S | 2/2016 | Chen |
| 9,247,773 B2 | 2/2016 | Memari et al. |
| D751,984 S | 3/2016 | Lin |
| D752,284 S | 3/2016 | Doster |
| D752,286 S | 3/2016 | Doster |
| D753,336 S | 4/2016 | Chen |
| 9,301,545 B2 | 4/2016 | Li et al. |
| D758,004 S | 5/2016 | Freshwater et al. |
| D758,651 S | 6/2016 | Wu |
| D758,655 S | 6/2016 | Freshwater et al. |
| D758,656 S | 6/2016 | Freshwater et al. |
| D759,303 S | 6/2016 | Afridi |
| D760,429 S | 6/2016 | Emarlou |
| D760,645 S | 7/2016 | Chen |
| D760,948 S | 7/2016 | Eksouzian |
| D761,999 S | 7/2016 | Liu |
| D762,003 S | 7/2016 | Lomeli |
| D764,703 S | 8/2016 | Liu |
| D767,821 S | 9/2016 | Clark et al. |
| D768,068 S | 10/2016 | Chen |
| D769,520 S | 10/2016 | Hua |
| D770,678 S | 11/2016 | Shin |
| D771,308 S | 11/2016 | Saydar et al. |
| D771,867 S | 11/2016 | Leidel et al. |
| D772,477 S | 11/2016 | Shin |
| D772,480 S | 11/2016 | Hua |
| D773,114 S | 11/2016 | Leidel et al. |
| D773,115 S | 11/2016 | Liu |

(56) References Cited

U.S. PATENT DOCUMENTS

| | | |
|---|---|---|
| D773,116 S | 11/2016 | Liu et al. |
| 9,498,000 B2 | 11/2016 | Kuczaj |
| D774,247 S | 12/2016 | Chen |
| D775,414 S | 12/2016 | Ampolini et al. |
| D775,762 S | 1/2017 | Chen |
| D776,337 S | 1/2017 | Levin et al. |
| D776,338 S | 1/2017 | Lomeli |
| D776,869 S | 1/2017 | Heidl |
| D778,492 S | 2/2017 | Liu |
| D778,493 S | 2/2017 | Scott |
| D779,719 S | 2/2017 | Qiu |
| D780,373 S | 2/2017 | Bennett et al. |
| D784,610 S | 4/2017 | Bosch |
| D786,497 S | 5/2017 | Sudlow et al. |
| D788,362 S | 5/2017 | Qiu |
| D788,363 S | 5/2017 | Chen |
| D788,364 S | 5/2017 | Chen |
| D788,697 S | 6/2017 | Verleur et al. |
| D789,598 S | 6/2017 | Chen |
| D790,122 S | 6/2017 | Hawes et al. |
| D790,123 S | 6/2017 | Beer et al. |
| D790,124 S | 6/2017 | Beer et al. |
| D790,125 S | 6/2017 | Beer et al. |
| D790,766 S | 6/2017 | Li |
| D792,020 S | 7/2017 | Mendoza |
| D792,021 S | 7/2017 | Beer et al. |
| D792,643 S | 7/2017 | Wong et al. |
| D792,644 S | 7/2017 | Jordan et al. |
| D796,112 S | 8/2017 | Lafferty et al. |
| D799,110 S | 10/2017 | Qiu |
| D799,111 S | 10/2017 | Qiu |
| D799,112 S | 10/2017 | Qiu |
| D799,113 S | 10/2017 | Qiu |
| D799,743 S | 10/2017 | Qiu |
| D799,744 S | 10/2017 | Qiu |
| D799,746 S | 10/2017 | Leidel et al. |
| D799,748 S | 10/2017 | Freese |
| D799,749 S | 10/2017 | Freese |
| D800,377 S | 10/2017 | Liu |
| D801,507 S | 10/2017 | Kelnhofer |
| D802,834 S | 11/2017 | Mathias et al. |
| D802,839 S | 11/2017 | Scott |
| 9,814,271 B2 | 11/2017 | Goggin et al. |
| D804,717 S | 12/2017 | Wang et al. |
| D805,685 S | 12/2017 | Lee |
| 9,833,021 B2 | 12/2017 | Perez et al. |
| D806,943 S | 1/2018 | Liu et al. |
| D807,286 S | 1/2018 | Qiu |
| D807,574 S | 1/2018 | Hawes et al. |
| D807,576 S | 1/2018 | Liu et al. |
| D807,577 S | 1/2018 | Ward et al. |
| D807,818 S | 1/2018 | Mathias et al. |
| D808,071 S | 1/2018 | Folkerts et al. |
| D808,073 S | 1/2018 | Leidel |
| D808,791 S | 1/2018 | Johnston et al. |
| D808,792 S | 1/2018 | Jaggi et al. |
| D809,191 S | 1/2018 | Li |
| D809,192 S | 1/2018 | Liu et al. |
| 9,861,135 B2 | 1/2018 | Chen |
| D814,693 S | 4/2018 | Qiu |
| D815,347 S | 4/2018 | Jones et al. |
| D816,895 S | 5/2018 | Ren |
| D818,636 S | 5/2018 | Qiu |
| 9,961,940 B2 | 5/2018 | Anderson, Jr. et al. |
| 9,968,136 B1 | 5/2018 | Bell |
| D819,880 S | 6/2018 | Qiu |
| D819,882 S | 6/2018 | Qiu |
| D821,639 S | 6/2018 | Dai et al. |
| D821,640 S | 6/2018 | Qiu |
| 9,999,258 B2 | 6/2018 | Newcomb et al. |
| D822,271 S | 7/2018 | Eksouzian |
| D822,272 S | 7/2018 | Miller et al. |
| D823,536 S | 7/2018 | Lai |
| D824,096 S | 7/2018 | Qiu |
| 10,028,532 B2 | 7/2018 | Zhu |
| 10,028,537 B1 | 7/2018 | Hawes et al. |
| 10,058,124 B2 | 8/2018 | Monsees et al. |
| D828,622 S | 9/2018 | Chen et al. |
| D828,953 S | 9/2018 | Chen |
| D831,270 S | 10/2018 | Qiu |
| D832,501 S | 10/2018 | Qiu et al. |
| 10,085,481 B2 | 10/2018 | Verleur et al. |
| 10,104,913 B2 | 10/2018 | Lau et al. |
| D833,063 S | 11/2018 | Qiu |
| D834,746 S | 11/2018 | Liu et al. |
| 10,117,460 B2 | 11/2018 | Sears et al. |
| 10,117,467 B2 | 11/2018 | Hawes et al. |
| D836,831 S | 12/2018 | Cividi |
| D842,237 S | 3/2019 | Qiu et al. |
| D844,232 S | 3/2019 | Qiu |
| D846,796 S | 4/2019 | Pan |
| D846,798 S | 4/2019 | Chen |
| 10,299,517 B2 | 5/2019 | Hawes et al. |
| D850,714 S | 6/2019 | Guo |
| D852,409 S | 6/2019 | Takehara |
| 10,327,474 B2 * | 6/2019 | Hawes .................... A24F 40/42 |
| D854,236 S | 7/2019 | Qiu |
| D854,741 S | 7/2019 | Smith |
| 10,375,990 B2 | 8/2019 | Lord |
| 10,485,269 B2 | 11/2019 | Hawes et al. |
| 10,492,541 B2 | 12/2019 | Lau et al. |
| D874,059 S | 1/2020 | Bailey et al. |
| 10,609,958 B2 | 4/2020 | Robinson et al. |
| 10,671,031 B2 | 6/2020 | Hawes et al. |
| 10,701,981 B2 | 7/2020 | Newcomb et al. |
| D919,172 S | 5/2021 | Zu |
| 11,013,273 B2 | 5/2021 | Newcomb et al. |
| D929,651 S | 8/2021 | Powell et al. |
| D936,279 S | 11/2021 | Israel et al. |
| 11,357,934 B2 * | 6/2022 | Hawes .................... A61M 15/06 |
| 11,752,283 B2 * | 9/2023 | Atkins .................. H02J 7/0034 |
| | | 131/329 |
| 11,877,595 B2 * | 1/2024 | Tucker ................. H05B 1/0244 |
| 12,076,482 B2 * | 9/2024 | Ampolini ................. H05B 3/03 |
| 12,082,623 B2 * | 9/2024 | Lomas .................... A24F 40/40 |
| 2005/0016550 A1 | 1/2005 | Katase |
| 2005/0268911 A1 | 12/2005 | Cross et al. |
| 2008/0023003 A1 | 1/2008 | Rosenthal |
| 2008/0092912 A1 | 4/2008 | Robinson et al. |
| 2009/0266358 A1 | 10/2009 | Sacristan Rock et al. |
| 2009/0293888 A1 | 12/2009 | Williams et al. |
| 2009/0293892 A1 | 12/2009 | Williams et al. |
| 2011/0011396 A1 | 1/2011 | Fang |
| 2011/0036346 A1 | 2/2011 | Cohen et al. |
| 2011/0265806 A1 | 11/2011 | Alarcon et al. |
| 2011/0277760 A1 | 11/2011 | Terry et al. |
| 2012/0174914 A1 | 7/2012 | Pirshafiey et al. |
| 2012/0199663 A1 | 8/2012 | Qiu |
| 2012/0272194 A1 | 10/2012 | Yang et al. |
| 2012/0318882 A1 | 12/2012 | Abehasera |
| 2013/0042865 A1 | 2/2013 | Monsees et al. |
| 2013/0081642 A1 | 4/2013 | Safari |
| 2013/0087160 A1 | 4/2013 | Gherghe |
| 2013/0167853 A1 | 7/2013 | Liu |
| 2013/0182360 A1 | 7/2013 | Stevens et al. |
| 2013/0192615 A1 | 8/2013 | Tucker et al. |
| 2013/0213418 A1 | 8/2013 | Tucker et al. |
| 2013/0220315 A1 | 8/2013 | Conley et al. |
| 2013/0228191 A1 | 9/2013 | Newton |
| 2013/0284192 A1 | 10/2013 | Peleg et al. |
| 2013/0298905 A1 | 11/2013 | Levin et al. |
| 2013/0327327 A1 | 12/2013 | Edwards et al. |
| 2013/0340775 A1 | 12/2013 | Juster et al. |
| 2013/0341218 A1 | 12/2013 | Liu |
| 2014/0007891 A1 | 1/2014 | Liu |
| 2014/0096781 A1 | 4/2014 | Sears et al. |
| 2014/0096782 A1 * | 4/2014 | Ampolini ................. A24F 40/60 |
| | | 131/328 |
| 2014/0107815 A1 | 4/2014 | LaMothe |
| 2014/0123989 A1 | 5/2014 | LaMothe |
| 2014/0123990 A1 | 5/2014 | Timmermans |
| 2014/0144453 A1 | 5/2014 | Capuano et al. |
| 2014/0150785 A1 | 6/2014 | Malik et al. |
| 2014/0157583 A1 | 6/2014 | Ward et al. |

(56) References Cited

U.S. PATENT DOCUMENTS

| | | |
|---|---|---|
| 2014/0174459 A1 | 6/2014 | Burstyn |
| 2014/0190830 A1 | 7/2014 | Sturmer et al. |
| 2014/0202474 A1 | 7/2014 | Peleg et al. |
| 2014/0224267 A1 | 8/2014 | Levitz et al. |
| 2014/0246035 A1 | 9/2014 | Minskoff et al. |
| 2014/0251326 A1 | 9/2014 | Terry et al. |
| 2014/0253144 A1 | 9/2014 | Novak, III et al. |
| 2014/0261408 A1 | 9/2014 | DePiano et al. |
| 2014/0261495 A1 | 9/2014 | Novak, III et al. |
| 2014/0270727 A1 | 9/2014 | Ampolini et al. |
| 2014/0270730 A1 | 9/2014 | DePiano et al. |
| 2014/0299137 A1 | 10/2014 | Kieckbusch et al. |
| 2014/0299141 A1 | 10/2014 | Flick |
| 2014/0338685 A1* | 11/2014 | Amir ............... H05B 1/0244 131/329 |
| 2014/0345635 A1 | 11/2014 | Rabinowitz et al. |
| 2014/0355969 A1 | 12/2014 | Stern |
| 2014/0360517 A1 | 12/2014 | Taggart et al. |
| 2014/0366898 A1 | 12/2014 | Monsees et al. |
| 2014/0378790 A1 | 12/2014 | Cohen |
| 2015/0013700 A1 | 1/2015 | Liu |
| 2015/0027455 A1 | 1/2015 | Peleg et al. |
| 2015/0040929 A1 | 2/2015 | Hon |
| 2015/0053217 A1 | 2/2015 | Steingraber et al. |
| 2015/0059786 A1 | 3/2015 | Li et al. |
| 2015/0075546 A1 | 3/2015 | Kueny, Sr. et al. |
| 2015/0082859 A1 | 3/2015 | Xiang |
| 2015/0101625 A1 | 4/2015 | Newton et al. |
| 2015/0108019 A1 | 4/2015 | Liu |
| 2015/0114410 A1 | 4/2015 | Doster |
| 2015/0128967 A1 | 5/2015 | Robinson et al. |
| 2015/0128971 A1 | 5/2015 | Verleur et al. |
| 2015/0128976 A1 | 5/2015 | Verleur et al. |
| 2015/0136124 A1* | 5/2015 | Aronie ............ A61M 15/0021 128/202.21 |
| 2015/0136158 A1 | 5/2015 | Stevens et al. |
| 2015/0142387 A1 | 5/2015 | Alarcon et al. |
| 2015/0164430 A1 | 6/2015 | Hu et al. |
| 2015/0181934 A1 | 7/2015 | Lyubomirskiy et al. |
| 2015/0189919 A1 | 7/2015 | Liu |
| 2015/0208729 A1 | 7/2015 | Monsees et al. |
| 2015/0237917 A1 | 8/2015 | Lord |
| 2015/0237918 A1 | 8/2015 | Liu |
| 2015/0257445 A1 | 9/2015 | Henry, Jr. et al. |
| 2015/0282527 A1 | 10/2015 | Henry, Jr. |
| 2015/0313287 A1 | 11/2015 | Verleur et al. |
| 2015/0320116 A1 | 11/2015 | Bleloch et al. |
| 2015/0328415 A1 | 11/2015 | Minskoff et al. |
| 2015/0342256 A1 | 12/2015 | Chen |
| 2015/0351456 A1 | 12/2015 | Johnson et al. |
| 2015/0367366 A1 | 12/2015 | Edwards et al. |
| 2015/0374039 A1 | 12/2015 | Zhu |
| 2016/0000149 A1 | 1/2016 | Scatterday |
| 2016/0029698 A1 | 2/2016 | Xiang |
| 2016/0089508 A1 | 3/2016 | Smith et al. |
| 2016/0120218 A1 | 5/2016 | Schennum et al. |
| 2016/0158782 A1 | 6/2016 | Henry, Jr. et al. |
| 2016/0309787 A1 | 10/2016 | Hawes et al. |
| 2016/0309788 A1 | 10/2016 | Hawes et al. |
| 2016/0345626 A1 | 12/2016 | Wong et al. |
| 2016/0353805 A1 | 12/2016 | Hawes et al. |
| 2016/0360789 A1 | 12/2016 | Hawes et al. |
| 2017/0006918 A1 | 1/2017 | Chen et al. |
| 2017/0013883 A1 | 1/2017 | Han et al. |
| 2017/0042246 A1 | 2/2017 | Lau et al. |
| 2017/0108840 A1 | 4/2017 | Hawes et al. |
| 2017/0119044 A1 | 5/2017 | Oligschlaeger et al. |
| 2017/0127979 A1 | 5/2017 | Azaria et al. |
| 2017/0181470 A1 | 6/2017 | Li |
| 2017/0188946 A1 | 7/2017 | Klusmann et al. |
| 2017/0208863 A1 | 7/2017 | Davis et al. |
| 2017/0208864 A1 | 7/2017 | Anderson, Jr. et al. |
| 2017/0215478 A1 | 8/2017 | Harrison et al. |
| 2017/0215479 A1 | 8/2017 | Kies |
| 2017/0245550 A1 | 8/2017 | Freelander |
| 2017/0290371 A1 | 10/2017 | Davis et al. |
| 2017/0295844 A1 | 10/2017 | Thevenaz et al. |
| 2017/0360092 A1 | 12/2017 | Althorpe et al. |
| 2017/0360098 A1 | 12/2017 | Newcomb et al. |
| 2017/0367406 A1 | 12/2017 | Schuler et al. |
| 2017/0367407 A1 | 12/2017 | Althorpe et al. |
| 2017/0369219 A1 | 12/2017 | Bailey et al. |
| 2018/0007954 A1 | 1/2018 | Mishra et al. |
| 2018/0007967 A1 | 1/2018 | Davis et al. |
| 2018/0013175 A1 | 1/2018 | Liu |
| 2018/0020738 A1 | 1/2018 | Qiu |
| 2018/0035715 A1 | 2/2018 | Wu |
| 2018/0070638 A1 | 3/2018 | Qiu |
| 2018/0084828 A1 | 3/2018 | Phillips et al. |
| 2018/0084836 A1 | 3/2018 | Perez et al. |
| 2018/0098571 A1 | 4/2018 | Watson |
| 2018/0110943 A1 | 4/2018 | Raichman |
| 2018/0116281 A1 | 5/2018 | Anderson, Jr. |
| 2018/0132526 A1 | 5/2018 | Davis et al. |
| 2018/0153219 A1 | 6/2018 | Verleur et al. |
| 2018/0160739 A1 | 6/2018 | Chen |
| 2018/0166238 A1 | 6/2018 | Chen |
| 2018/0279682 A1 | 10/2018 | Guo et al. |
| 2019/0008208 A1 | 1/2019 | Cirillo et al. |
| 2021/0153548 A1 | 5/2021 | Twite et al. |
| 2021/0153564 A1 | 5/2021 | Hourmand et al. |
| 2021/0153567 A1 | 5/2021 | Twite et al. |
| 2021/0219621 A1 | 7/2021 | Parrott et al. |
| 2021/0219622 A1 | 7/2021 | Parrott et al. |

FOREIGN PATENT DOCUMENTS

| | | |
|---|---|---|
| CN | 202738815 U | 2/2013 |
| CN | 202890462 U | 4/2013 |
| CN | 202919035 U | 5/2013 |
| CN | 202919036 U | 5/2013 |
| CN | 203087525 U | 7/2013 |
| CN | 203341011 U | 12/2013 |
| CN | 203446537 U | 2/2014 |
| CN | 203457810 U | 3/2014 |
| CN | 203646502 U | 6/2014 |
| CN | 104026746 A | 9/2014 |
| CN | 203828071 U | 9/2014 |
| CN | 203841122 U | 9/2014 |
| CN | 203841124 U | 9/2014 |
| CN | 203851805 U | 10/2014 |
| CN | 203986094 U | 12/2014 |
| CN | 203986106 U | 12/2014 |
| CN | 204070533 U | 1/2015 |
| CN | 204070549 U | 1/2015 |
| CN | 204104844 U | 1/2015 |
| CN | 204146307 U | 2/2015 |
| CN | 104432537 A | 3/2015 |
| CN | 204234255 U | 4/2015 |
| CN | 204259818 U | 4/2015 |
| CN | 106820274 A | 6/2017 |
| CN | 303417607 S | 6/2017 |
| CN | 206413749 U | 8/2017 |
| EM | 002337410-0013 | 11/2013 |
| EP | 0640297 A1 | 3/1995 |
| EP | 3285844 B1 | 7/2019 |
| GB | 2502164 A | 11/2013 |
| JP | 2011-505874 A | 3/2011 |
| JP | 1421818 | 8/2011 |
| JP | 2016-508743 A | 3/2016 |
| JP | 1584539 S | 8/2017 |
| KR | 2011-0006928 U | 7/2011 |
| KR | 20130031550 A | 3/2013 |
| KR | 101465034 B1 | 11/2014 |
| KR | 10-1516309 | 5/2015 |
| RU | 00104198 | 7/2017 |
| WO | WO-2009/079641 A2 | 6/2009 |
| WO | WO-2013040193 A2 | 3/2013 |
| WO | WO-2014/060267 A2 | 4/2014 |
| WO | WO-2014/060269 A1 | 4/2014 |
| WO | WO-2014/066730 A1 | 5/2014 |
| WO | WO-2014/095737 A1 | 6/2014 |
| WO | WO-2014/110119 A1 | 7/2014 |
| WO | WO-2014/125483 A1 | 8/2014 |

(56) References Cited

FOREIGN PATENT DOCUMENTS

| | | |
|---|---|---|
| WO | WO-2014/139609 A2 | 9/2014 |
| WO | WO-2014-144678 A2 | 9/2014 |
| WO | 2014/205749 A1 | 12/2014 |
| WO | WO-2014207719 A1 | 12/2014 |
| WO | WO-2015031836 A1 | 3/2015 |
| WO | WO-2015052513 A2 | 4/2015 |
| WO | WO-2015/077645 A1 | 5/2015 |
| WO | WO-2015/100361 A1 | 7/2015 |
| WO | WO-2015/131991 A1 | 9/2015 |
| WO | WO-2015/189556 A1 | 12/2015 |
| WO | WO-2015/197165 A1 | 12/2015 |
| WO | WO-2016/009202 A1 | 1/2016 |
| WO | WO-2016/100368 A1 | 6/2016 |
| WO | WO-2016/172023 A1 | 10/2016 |

OTHER PUBLICATIONS

U.S. Notice of Allowance dated Nov. 30, 2022 for corresponding U.S. Appl. No. 17/352,781.
Notification of Defects dated Feb. 5, 2023 issued in related Israeli patent application No. 254728.
Notice of Allowance for corresponding U.S. Appl. No. 18/190,357 mailed Aug. 9, 2023.
International Search Report and Written Opinion dated Jul. 19, 2016.
International Preliminary Report on Patentability dated Oct. 24, 2017.
Parate, "Designing Efficient and Accurate Behavior-Aware Mobile Systems," Doctoral Dissertations, University of Massachusetts-Amherst, 2014.
International Search Report and Written Opinion dated Mar. 29, 2018.
Office Action for U.S. Appl. No. 15/135,932 mailed on Mar. 14, 2018.
Office Action for U.S. Appl. No. 15/135,932 mailed on Sep. 18, 2018.
Notice of Allowance for U.S. Appl. No. 15/135,932 mailed on Feb. 26, 2019.
Web address http://www.my7s.com/faq, 7's electronic cigarettes, Electronic Vapor.
International Search Report dated Jun. 23, 2016, issued in corresponding International Application No. PCT/US2016/028048.
Written Opinion of the International Searching Authority dated Jun. 23, 2016, issued in corresponding International Application No. PCT/US2016/028048.
U.S. Office Action dated Jun. 5, 2017 for copending U.S. Appl. No. 14/998,020.
Viva—retrieved on Sep. 18, 2017 at https://cdn.shopify.com/s/files/1/1203/8500/products/viva-vaporizer-01_large.jpg?v=1480032844.
ALD—retrieved Sep. 18, 2017 at https://ae01.alicdn.com/kf/HTB1gMOmPFXXXXbdXpXXq6xXFXXXR/ALD-AMAZE-dry-herb-vaporizer-font-b-kit-b-font-smoke-herbal-electronic-cigarette-vaporizer-portable.jpg.
International Search Report and Written Opinion for Application No. PCT/US2016/028048 dated Nov. 2, 2017.
Office Action for corresponding U.S. Appl. No. 14/998,020 dated Dec. 21, 2017.
Office Action for corresponding U.S. Appl. No. 15/334,989 dated Feb. 23, 2018.
Notice of Allowance for corresponding U.S. Appl. No. 15/601,365 dated Mar. 2, 2018.
VaporDNA by VaporDNA dated 2013-2018, found online https://www.vapordna.com/SMPO-Ultra-Portable-Kit-p/smpoup.htm?Click=40939.
Vype Bye Electronic Tobacconist dated 2018, found online https://www.electrictobacconist.co.uk/vype-pebble-p7009.
Notice of Allowance for corresponding U.S. Appl. No. 29/575,887 dated May 3, 2018.
Notice of Allowance for corresponding U.S. Appl. No. 29/575,883 dated May 3, 2018.
Notice of Allowance for corresponding U.S. Appl. No. 15/911,533 dated May 8, 2018.
Non-Final Office Action for corresponding U.S. Appl. No. 15/984,627 dated Jul. 12, 2018.
Notice of Allowance for corresponding U.S. Appl. No. 29/623,426 dated Jul. 19, 2018.
Notice of Allowance for corresponding U.S. Appl. No. 29/623,423 dated Jul. 24, 2018.
Office Action for corresponding U.S. Appl. No. 16/010,934 dated Aug. 7, 2018.
Notice of Allowance dated Aug. 29, 2018 issued in corresponding U.S. Appl. No. 29/575,881.
Office Action dated Sep. 11, 2018 issued in corresponding U.S. Appl. No. 29/575,895.
U.S. Office Action dated Oct. 4, 2018 for co-pending U.S. Appl. No. 16/111,468.
European Office Action issued Oct. 10, 2018 in corresponding Application No. 18178672.4.
U.S. Office Action dated Dec. 13, 2018 for corresponding U.S. Appl. No. 16/160,110.
Office Action for corresponding U.S. Appl. No. 29/575,881 dated Feb. 25, 2019.
U.S. Office Action for corresponding U.S. Appl. No. 29/575,895 dated Mar. 1, 2019.
United States Notice of Allowance for corresponding U.S. Appl. No. 16/111,468, dated Apr. 18, 2019.
United States Office Action for corresponding U.S. Appl. No. 16/166,899, dated Apr. 18, 2019.
Office Action for corresponding Eurasian Application No. 201792097 dated Apr. 23, 2019 and English translation thereof.
Eurasian Office Action for corresponding Application No. 201792097 dated May 7, 2019, English translation thereof.
United States Office Action for corresponding U.S. Appl. No. 29/670,492 dated May 23, 2019.
Smokio, http://www.premiumlifestyle.co.uk/products/smokio-smart-wireless-e-cigarette, 2014.
Go Electronic Cigarette, "Igo 4Electronic Cigarette," http://www.electronic-cigarette.ie/Charger-iGO4, Feb. 19, 2015.
United States Notice of Allowance for corresponding U.S. Appl. No. 16/166,899, dated Jul. 10, 2019.
United States Notice of Allowance for corresponding U.S. Appl. No. 16/111,468, dated Jul. 10, 2019.
United States Notice Of Allowance for corresponding U.S. Appl. No. 29/575,881, dated Jul. 17, 2019.
Examination Report for European Application No. 16 721 308.1 dated Jul. 9, 2019.
Notice of Allowance for U.S. Appl. No. 29/670,492 dated Sep. 30, 2019.
Eurasian Office Action for corresponding Application No. 201792100 mailed Jun. 27, 2019.
United States Notice Of Allowance for U.S. Appl. No. 29/670,492, dated Sep. 30, 2019.
United States Office Action for U.S. Appl. No. 16/425,168, dated Oct. 3, 2019.
U.S. Office Action for corresponding U.S. Appl. No. 15/390,810 mailed Oct. 23, 2019.
U.S. Notice of Allowance dated Nov. 5, 2019 for corresponding U.S. Appl. No. 16/395,614.
Chinese Office Action dated Oct. 11, 2019 for corresponding Chinese Application No. 201680023188.9.
Chinese Office Action for corresponding Application No. 201680035173.4, dated Sep. 27, 2019, English translation thereof.
Chinese Office Action for corresponding Application No. 201680023188.9, dated Oct. 11, 2019, English translation thereof.
U.S. Notice of Allowance for corresponding U.S. Appl. No. 15/390,810 mailed Feb. 10, 2020.
Eurasian Office Action mailed Jan. 21, 2020 in Eurasian Application No. 201792100.
European Office Action dated Feb. 24, 2020 for corresponding European Application No. 18178672.4.

(56) References Cited

OTHER PUBLICATIONS

Eurasian Office Action for corresponding Application No. 201792100, dated Mar. 6, 2020, English translation thereof.
United States Notice of Allowance for U.S. Appl. No. 16/425,168, dated Mar. 11, 2020.
U.S. Notice of Allowance for corresponding U.S. Appl. No. 29/677,918 mailed Apr. 15, 2020.
Ukrainian Office Action and English translation thereof dated Mar. 26, 2020.
Ukrainian Office Action for corresponding Application No. a201710002, dated Mar. 11, 2020, English translation thereof.
Ukrainian Office Action and English translation thereof mailed Apr. 13, 2020.
Eurasian Office Action for corresponding Application No. a201911670, dated Apr. 13, 2020.
Office Action for Malaysian Application No. PI 2017001565 dated Jun. 23, 2020.
U.S. Notice of Allowance for corresponding U.S. Appl. No. 29/677,918 mailed Jul. 6, 2020.
Israeli Office Action dated Jun. 29, 2020 issued in Israeli Patent Application No. 255080. English translation has been provided.
Extended European Search Report for Application No. 17885846.0-1004, dated Jul. 27, 2020.
Office Action for corresponding U.S. Appl. No. 16/746,001 dated Aug. 6, 2020.
Office Action for Chinese Application No. 201680023188.9 dated Aug. 3, 2020 and English translation.
Parate, A., "Designing Efficient and Accurate Behavior-Aware Mobile Systems," Nov. 2014.
Eurasian Office Action mailed Aug. 28, 2020.
Notice of Allowance for U.S. Appl. No. 29/677,918 dated Aug. 21, 2020.
Modified Substantive Examination Adverse Report for Malaysian Patent Application No. PI 2017001568 dated Sep. 9, 2020.
U.S. Notice of Allowance for corresponding U.S. Appl. No. 29/677,918 mailed Sep. 28, 2020.
U.S. Notice of Allowance dated Oct. 27, 2020 for corresponding U.S. Appl. No. 29/677,918.
Eurasian Office Action mailed Oct. 22, 2020.
This Might Just Be The First Great E-Cig, Wired, Apr. 21, 2015.
PAX Labs, Inc. Introduces Revolutionary Technologies with Powerful ECigarette Juul, Business Wire, Apr. 21, 2015.
Startup behind the Lambo of vaporizers just launched an intelligent e-cigarette, The Verge, Apr. 21, 2015.
Vaporization Startup Pax Labs Introduces Juul, Its Next Gen E-Cigarette, Tech Crunch, Apr. 21, 2015.
JWell Inova 1.0 Pod System ("Inova 1.0"), https://www.youtube.com/watch?v=hTfwGal9LJM and https://www.vape.museum/vape/jwellinova-1-0-pod-system.
JWell Inova 2.0 Pod System ("Inova 2.0"), https://www.youtube.com/watch?v=0RdshN5RAC8&fbclid=IWAR1l_xU3VAVVZaKXoeDFqrCUXXOkpZCJil1oj3gRUhKll9vmp-gRFm0w9bA.
InnokiniTaste/iWand System ("Innokin"), https://www.youtube.com/watch?v=5b8vU72buD8 (Video 1); https://www.youtube.com/watch?v=ejiWtKu6HVM (Video 2); https://www.youtube.com/watch?v=zOaLmN2orbs (Video 3); https://www.youtube.com/watch?v=mz414d8MU20 (Video 4); Innokin User Manual.
IPh-8 E-Cigarette System ("iPh-8"), https://www.youtube.com/watch?v=Y4Hg527EdF4; https://www.vape.museum/vape/iph-8-ecig.
CPHS1 System/Kanger S1 System ("CPH-S1"), https://www.youtube.com/watch?v=06YeAZiNhs8.
Ijoy SS Itop System ("Ijoy"), https://web.archive.org/web/20130805124853/http://ijoycig.com/IJOY--ITOP400-p149.html; and https://www.youtube.com/watch?v=Ch_xgzIFXwU&has_verified=1.
Examination Report for Israeli Application No. 2547628 dated Jan. 18, 2021 and English translation.
Notice of Allowance for U.S. Appl. No. 16/746,001 dated Jan. 27, 2021.
U.S. Notice of Allowance dated Feb. 4, 2021 for corresponding U.S. Appl. No. 16/887,147.
Notice of Allowance for U.S. Appl. No. 16/746,001 dated Feb. 22, 2021.
U.S. Notice of Allowance dated Apr. 14, 2021 for corresponding U.S. Appl. No. 17/176,520.
Eurasian Office Action for corresponding Application No. 201991581 issued on Apr. 13, 2021 and English translation thereof.
U.S. Notice of Allowance for corresponding U.S. Appl. No. 16/661,235 mailed May 4, 2021.
Office Action for corresponding U.S. Appl. No. 16/441,086 dated May 7, 2021.
Chinese Office Action and English translation thereof dated Jun. 2, 2021 for corresponding Chinese Application No. 201880033617.
Third Party Observation dated Jun. 9, 2021 for corresponding European Application No. 18732954.5.
European Office Action for corresponding European Application No. 18732954.5 mailed Sep. 14, 2021.
U.S. Office Action dated Oct. 22, 2021 for corresponding U.S. Appl. No. 16/441,086.
Eurasian Office Action dated Dec. 13, 2021 for corresponding Eurasian Application No. 201991581.
Vaping Device By: Juul found online (Jan. 25, 2022); https://www.nextgenerationvillage.com/drugs/vaping/faq/are-vaping-and-juuling-the-same/ (2018).
U.S. Election of Species Requirement for corresponding U.S. Appl. No. 29/671,354 mailed Jan. 31, 2022.
Eurasian Office Action mailed Jan. 27, 2022.
Chinese Office Action and English translation thereof dated Jan. 30, 2022.
Israeli Office Action dated Feb. 9, 2022 for corresponding Israeli Application No. 254728, and English-language translation thereof.
Office Action for Chinese Application No. 201880033617.X dated Jan. 30, 2022 and English translation.
Office Action for Eurasian Application No. 202191925 mailed Feb. 14, 2022 and English translation.
Notice of Allowance dated Feb. 24, 2022 issued in corresponding U.S. Appl. No. 16/441,086.
Office Action dated Feb. 23, 2022 issued in corresponding Israeli Patent Application No. 267664.
Office Action dated Feb. 18, 2022 issued in corresponding Ukrainian Patent Application No. A201908951.
European Third Party Observation mailed Mar. 3, 2022.
European Examination Report dated May 6, 2022.
Israeli Notice of Deficiencies for Patent Application mailed Sep. 11, 2022.
European Communication pursuant to Rule 114(2) mailed Sep. 21, 2022.
U.S. Office Action dated Sep. 29, 2022 for corresponding U.S. Appl. No. 17/352,781.
U.S. Notice of Allowance dated Oct. 4, 2022 for corresponding U.S. Appl. No. 29/671,354.
Malaysian Modified Examination Adverse Report mailed Sep. 30, 2022.
U.S. Notice of Allowance for corresponding U.S. Appl. No. 18/480,241 mailed May 1, 2024.
U.S. Notice of Allowance for U.S. Appl. No. 29/770,338, dated Jul. 12, 2024.
U.S. Notice of Allowance for U.S. Appl. No. 18/468,112, dated Aug. 15, 2024.
Notice of Allowance dated Sep. 5, 2024 issued in U.S. Appl. No. 29/869,920.
Israeli Notice of Deficiencies for Israeli Application No. 309409 mailed Sep. 30, 2024.
Chinese Office Action and English translation thereof for Chinese Application No. 202110061064.2 mailed Nov. 8, 2024.
Notice of Allowance dated Jan. 2, 2025 issued in U.S. Appl. No. 29/869,920.

(56) References Cited

OTHER PUBLICATIONS

Chinese Office Action and English translation thereof for Chinese Application No. 202110061064.2 mailed Feb. 20, 2025.

\* cited by examiner

108

110

112

118

120

208

209

POD ASSEMBLY, DISPENSING BODY, AND E-VAPOR APPARATUS INCLUDING THE SAME

PRIORITY

This non-provisional patent application is a continuation of, and claims priority under 35 U.S.C. § 120 to U.S. application Ser. No. 16/441,086, filed Jun. 14, 2019, which claims priority under 35 U.S.C. § 120 to U.S. application Ser. No. 15/135,932, filed Apr. 22, 2016, which claims priority under 35 U.S.C. § 119(e) to provisional U.S. Application No. 62/151,160 filed on Apr. 22, 2015 and 62/151,179 filed on Apr. 22, 2015, the entire contents of each of which are incorporated herein by reference.

BACKGROUND

Field

The present disclosure relates to electronic vapor devices including self-contained articles including pre-vapor formulations.

Description of Related Art

Electronic vaping devices are used to vaporize a pre-vapor formulation material into a vapor. These electronic vaping devices may be referred to as e-vaping devices. E-vaping devices include a heater which vaporizes the pre-vapor formulation material to produce vapor. An e-vaping device may include several e-vaping elements including a power source, a cartridge or e-vaping tank including the heater and along with a reservoir capable of holding the pre-vapor formulation material.

SUMMARY

At least some example embodiments relate to an e-vaping device.

At least one example embodiment discloses a pod for an electronic vapor (e-vapor) apparatus. The pod includes a pre-vapor formulation compartment configured to hold a pre-vapor formulation therein, a device compartment in fluidic communication with the pre-vapor formulation compartment, the device compartment including a processor configured to monitor the pre-vapor formulation compartment and identify the pre-vapor formulation and a vapor channel extending from the device compartment and through the pre-vapor formulation compartment.

In an example embodiment, a surface of the pod includes at least one electrical contact coupled to the processor.

In an example embodiment, the at least one electrical contact is configured to couple the pod to a battery of the e-vapor apparatus.

In an example embodiment, the processor is configured to provide energy information associated with the pod to the e-vapor apparatus.

In an example embodiment, the energy information is associated with a formulation of the pre-vapor formulation.

In an example embodiment, the device compartment further includes a memory device configured to store power information associated with the e-vapor apparatus.

In an example embodiment, the memory device is a programmable read only memory.

In an example embodiment, the processor is configured to authenticate the pod with respect to the e-vapor apparatus.

At least one example embodiment discloses an electronic vapor (e-vapor) apparatus including a pod including a pre-vapor formulation compartment, a device compartment, and a vapor channel extending from the device compartment and through the pre-vapor formulation compartment, the pre-vapor formulation compartment configured to hold a pre-vapor formulation therein and the device compartment including a processor configured to monitor the pre-vapor formulation compartment and identify the pre-vapor formulation and a dispensing body including a proximal portion and an opposing distal portion, the proximal portion including a vapor passage and receiving element, the vapor passage extending from an end surface of the proximal portion to a side wall of the receiving element, the receiving element being between the vapor passage and the distal portion of the dispensing body, the receiving element configured to receive the pod, and the processor configured to communicate with the dispensing body.

In an example embodiment, the dispensing body is configured to authenticate the pod based on communicating with the processor.

In an example embodiment, the device compartment of the pod includes a memory device.

In an example embodiment, the memory device includes an electronic signature to authenticate the pod.

In an example embodiment, the e-vapor apparatus further includes a vaporizer disposed in at least one of the pod and the dispensing body, the pre-vapor formulation compartment of the pod configured to be in fluidic communication with the vaporizer during an operation of the e-vapor apparatus such that the pre-vapor formulation from the pre-vapor formulation compartment comes into thermal contact with the vaporizer, the vaporizer configured to vaporize the pre-vapor formulation to produce a vapor that passes through the pod via the vapor channel, the through-hole of the dispensing body configured to receive the pod such that the vapor channel of the pod is aligned with the vapor passage of the dispensing body so as to facilitate a delivery of the vapor through the vapor passage of the dispensing body, and the processor is configured to communicate operational parameters of the vaporizer to the dispensing body.

In an example embodiment, the operational parameters correspond to a solution of the pre-vapor formulation.

In an example embodiment, the operational parameters include at least one of battery settings and energy settings.

In an example embodiment, the dispensing body is configured to perform at least one of supply power to and communicate with the pod via at least one electrical contact coupled to the processor.

In an example embodiment, the at least one electrical contact is on a side of the pod.

In an example embodiment, the processor is configured to receive usage data from the dispensing body.

In an example embodiment, the processor is configured to provide liquid usage parameters associated with the pod to the dispensing body.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
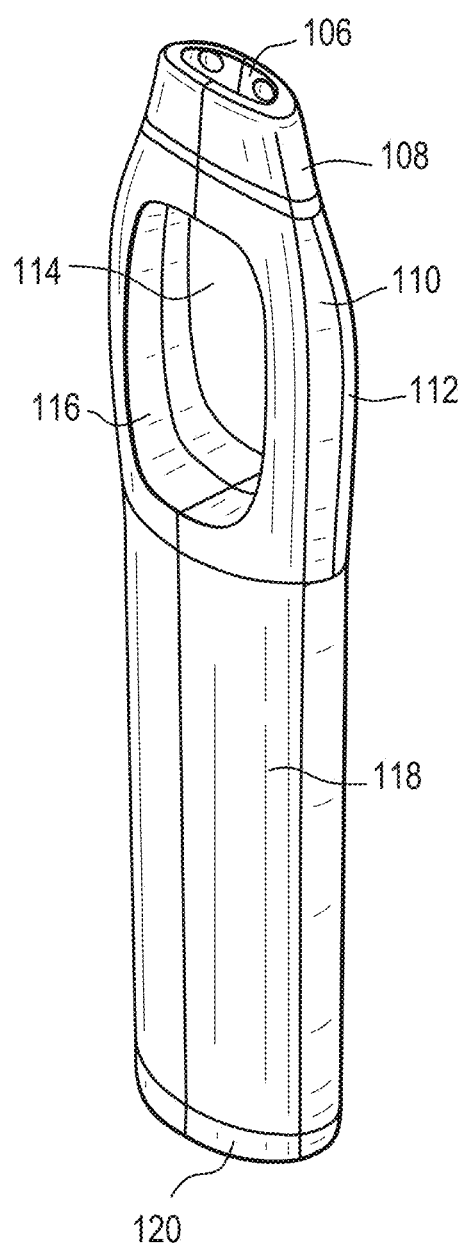
FIG. 1 is a perspective view of a dispensing body of an e-vapor apparatus according to an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. The regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 is a perspective view of a dispensing body of an e-vapor apparatus according to an example embodiment. Referring to FIG. 1, a dispensing body 104 of an e-vapor apparatus includes a frame portion that is connected to a body portion 118. The frame portion includes a first frame 110 and a second frame 112. The side walls 116 (e.g., inner side surfaces) of the first frame 110 and the second frame 112 define a through-hole 114. The through-hole 114 is configured to receive a pod assembly (which will be subsequently discussed in detail).

Generally, an e-vapor apparatus may include the dispensing body 104, a pod assembly inserted in the through-hole 114 of the dispensing body 104, and a vaporizer disposed in at least one of the pod assembly and the dispensing body 104. The pod assembly may include a pre-vapor formulation compartment (e.g., pre-vapor formulation compartment), a device compartment, and a vapor channel. The vapor channel may extend from the device compartment and traverse the pre-vapor formulation compartment. The pre-vapor formulation compartment is configured to hold a pre-vapor formulation (e.g., pre-vapor formulation) therein. A pre-vapor formulation is a material or combination of materials that may be transformed into a vapor. For example, the pre-vapor formulation may be a liquid, solid, and/or gel formulation including, but not limited to, water, beads, solvents, active ingredients, ethanol, plant extracts, natural or artificial flavors, and/or vapor formers such as glycerine and propylene glycol.

The dispensing body 104 includes a proximal portion and an opposing distal portion. The mouthpiece 108 is disposed at the proximal portion, while the end piece 120 is disposed at the distal portion. The proximal portion includes a vapor passage 106 and the through-hole 114. The vapor passage 106 extends from an end surface of the proximal portion to the side wall 116 of the through-hole 114. The vapor passage 106 is in the form of one or more passageways extending through the proximal portion of the dispensing body 104. The through-hole 114 is between the vapor passage 106 and the distal portion of the dispensing body 104 (e.g., between the mouthpiece 108 and the body portion 118).

A vaporizer (which will be subsequently discussed in more detail) is disposed in at least one of the pod assembly and the dispensing body 104. The pre-vapor formulation compartment of the pod assembly is configured to be in fluidic communication with the vaporizer during an operation of the e-vapor apparatus such that the pre-vapor formulation from the pre-vapor formulation compartment comes into thermal contact with the vaporizer. The vaporizer is configured to heat the pre-vapor formulation to produce a vapor that passes through the pod assembly via the vapor channel. The through-hole 114 of the dispensing body 104 is configured to receive the pod assembly such that the vapor channel of the pod assembly is aligned with the vapor passage 106 of the dispensing body 104 so as to facilitate a delivery of the vapor through the vapor passage 106 of the dispensing body 104.

Figure 2:
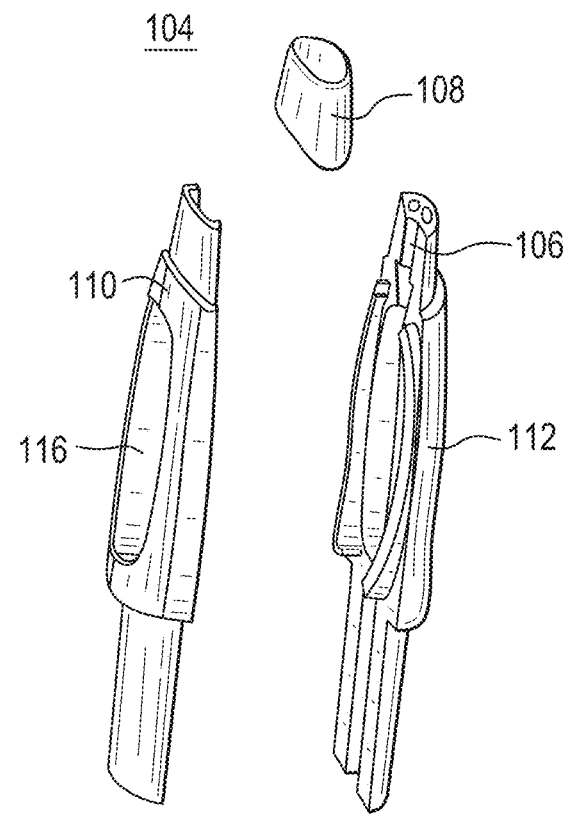
FIG. 2 is an exploded view of the dispensing body of FIG. 1.
Figure 2:
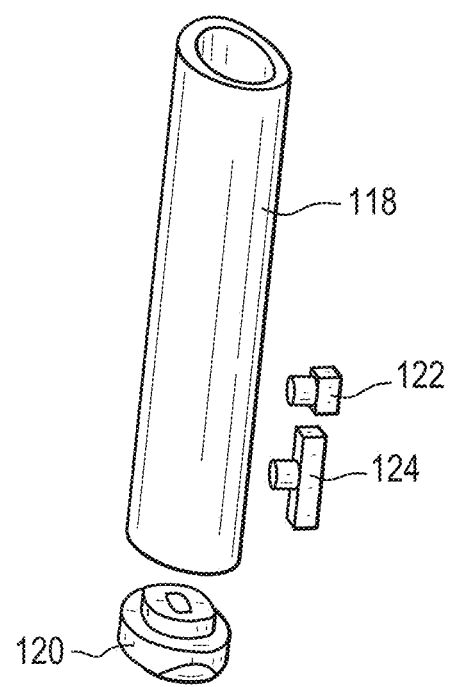

FIG. 2 is an exploded view of the dispensing body of FIG. 1. Referring to FIG. 2, the first frame 110 and the second frame 112 are configured to unite to form the frame portion of the dispensing body 104. A number of options are available for uniting the first frame 110 and the second frame 112. In an example embodiment, the first frame 110 is a female member, while the second frame 112 is a male member that is configured to engage therewith. Alternatively, the first frame 110 may be a male member, while the second frame 112 may be a female member that is configured to engage therewith. The engagement of the first frame 110 and the second frame 112 may be via a snap-fit, friction-fit, or slide-lock type arrangement, although example embodiments are not limited thereto.

The first frame 110 may be regarded as the front frame of the dispensing body 104, and the second frame 112 may be regarded as the rear frame (or vice versa). Additionally, the proximal ends of the first frame 110 and the second frame 112, when united, define the vapor passage 106 therebetween. The vapor passage 106 may be in the form of a single passageway that is in communication with the through-hole 114 defined by the side wall 116. Alternatively, the vapor passage 106 may be in the form of a plurality of passageways that are in communication with the through-hole 114 defined by the side wall 116. In such an example, the plurality of passageways may include a central passageway surrounded by peripheral passageways (or just several evenly spaced passageways). Each of the plurality of passageways may independently extend from the through-hole 114 to the proximal end surface of the frame portion. Alternatively, a common passageway may extend partly from the through-hole 114 and then branch into a plurality of passageways that extend to the proximal end surface of the frame portion.

The mouthpiece 108 is configured to slip onto the proximal end of the frame portion that defines the vapor passage 106. As a result, the outer surface of the proximal end formed by the first frame 110 and the second frame 112 may correspond to an inner surface of the mouthpiece 108. Alternatively, the proximal end defining the vapor passage 106 may be integrally formed as part of the mouthpiece 108 (instead of being a part of the frame portion). The mouthpiece 108 may be secured via a snap-fit type or other suitable arrangement. In an example embodiment, the mouthpiece 108 is a removable element that is intended to permit voluntary, recommended, or required replacement by an adult vaper. For instance, the mouthpiece 108 may, in addition to its intended functionality, provide a visual or other sensory appeal. In particular, the mouthpiece 108 may be formed of an ornamental material (e.g., wood, metal, ceramic) and/or include designs (e.g., patterns, images, characters). Moreover, the length of the mouthpiece 108 may be varied to adjust for the temperature at an outlet of the mouthpiece. Thus, the mouthpiece 108 may be customized so as to provide an expression of personality and individuality. In other instances, the removable nature of the mouthpiece 108 may facilitate a recommended replacement due to the amount of usage or a required replacement due to wear over time or damage (e.g., chipped mouthpiece 108 caused by accidental dropping of e-vapor apparatus).

The lower ends of the first frame 110 and the second frame 112 opposite the proximal ends (that define the vapor passage 106) are configured to insert into the body portion 118. To facilitate a secure fit, the outer surface of the lower ends of the first frame 110 and the second frame 112 may correspond to a receiving inner surface of the body portion 118. Additionally, the lower ends of the first frame 110 and the second frame 112 may also define a groove therebetween to accommodate one or more wires that connect to one or more electrical contacts provided in the side wall 116 (e.g., lower surface of the side wall 16 opposite the vapor passage 106). A power source (e.g., battery) may also be provided in the groove to supply the requisite current through the wire(s). Alternatively, the power source may be provided in an available space within the body portion 118 between the inserted lower end of the frame portion and the end piece 120.

A first button 122 and a second button 124 may be provided on the body portion 118 and connected to the corresponding circuitry and electronics therein. In an example embodiment, the first button 122 may be a power button, and the second button 124 may be a battery level indicator. The battery level indicator may display a representation of the amount of power available (e.g., 3 out of 4 bars). In addition, the battery level indicator may also blink and/or change colors. To stop the blinking, a second button 124 may be pressed. Thus, the button(s) of the e-vapor apparatus may have a control and/or display function. It should be understood that the examples with regard to the first button 122 and the second button 124 are not intended to be limiting and can have different implementations depending on the desired functionalities. Accordingly, more than two buttons (and/or of different shapes) may be provided in the same proximity or at a different location on the e-vapor apparatus. Moreover, different implementations of the first button 122 and the second button 124 may be controlled by a controller 2105 based on inputs from an adult vaper.

Figure 3:
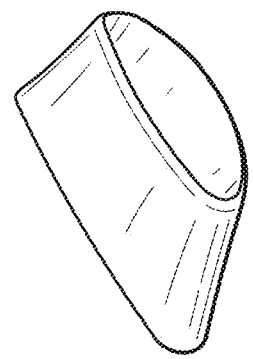
FIG. 3 is a perspective view of the mouthpiece of FIG. 2.

FIG. 3 is a perspective view of the mouthpiece of FIG. 2. Referring to FIG. 3, the mouthpiece 108 may be an open-ended cap-like structure that is configured to slip onto the proximal end of the frame portion defining the vapor passage 106. The mouthpiece 108 may have a wider base that tapers to a narrower top. However, it should be understood that example embodiments are not limited thereto. In an example embodiment, one side of the mouthpiece 108 may be more linear, while the opposing side may be more curved.

Figure 4:
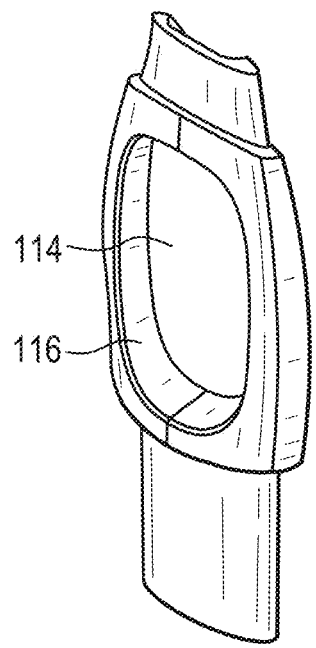
FIG. 4 is a perspective view of the first frame of FIG. 2.

FIG. 4 is a perspective view of the first frame of FIG. 2. Referring to FIG. 4, the first frame 110 includes a side wall 116 that defines a through-hole 114. The first frame 110 is configured to unite with the second frame 112, which also includes a side wall 116 defining a through-hole 114. Because the combined through-hole 114 is configured to receive a pod assembly, the side walls 116 of the first frame 110 and the second frame 112 may form a relatively smooth and continuous surface to facilitate the insertion of the pod assembly.

Figure 5:
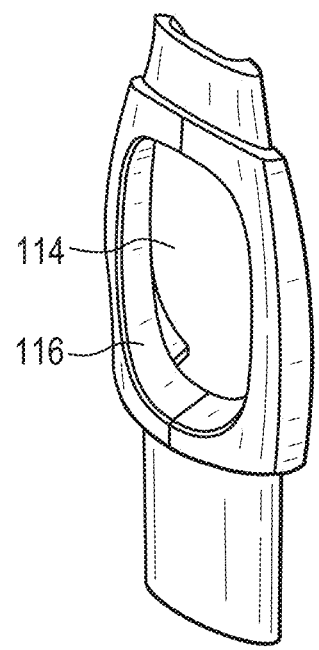
FIG. 5 is a perspective view of the second frame of FIG. 2.

FIG. 5 is a perspective view of the second frame of FIG. 2. Referring to FIG. 5, the second frame 112 is configured to unite with the first frame 110 such that the shape defined by the combined side walls 116 corresponds to the shape of the side surface of a pod assembly. In addition, an attachment structure (e.g., mating member/recess, magnetic arrangement) may be provided on at least one of the side walls 116 and the side surface of the pod assembly.

For example, the attachment structure may include a mating member that is formed on the side wall 116 (of the first frame 110 and/or second frame 112) and a corresponding recess that is formed on the side surface of the pod assembly. Conversely, the mating member may be formed on the side surface of the pod assembly, while the corresponding recess may be formed on the side wall 116 (of the first frame 110 and/or second frame 112). In a non-limiting embodiment, the mating member may be a rounded structure to facilitate the engagement/disengagement of the attachment structure, while the recess may be a concave indentation that corresponds to the curvature of the rounded structure. The mating member may also be spring-loaded so as to retract (via spring compression) when the pod assembly is being inserted into the through-hole 114 and protract (via spring decompression) when mating member becomes aligned with the corresponding recess. The engagement of the mating member with the corresponding recess may result in an audible click, which provides a notification that the pod assembly is secured and properly positioned within the through-hole 114 of the dispensing body 104.

In another example, the attachment structure may include a magnetic arrangement. For instance, a first magnet may be arranged in the side wall 116 (of the first frame 110 and/or second frame 112), and a second magnet may be arranged in the side surface of the pod assembly. The first and/or second magnets may be exposed or hidden from view behind a layer of material. The first and second magnets are oriented so as to be attracted to each other, and a plurality of pairs of the first and second magnets may be provided to ensure that the pod assembly will be secure and properly aligned within the through-hole 114 of the dispensing body 104. As a result, when the pod assembly is inserted in the through-hole 114, the pair(s) of magnets (e.g., first and second magnets) will be attracted to each other and, thus, hold the pod assembly within the through-hole 114 while properly aligning the channel outlet of the pod assembly with the vapor passage 106 of the dispensing body 104.

Figure 6:
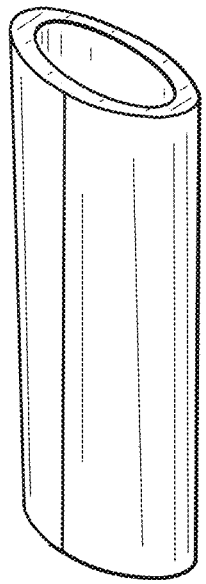
FIG. 6 is a perspective view of the body portion of FIG. 2.

FIG. 6 is a perspective view of the body portion of FIG. 2. Referring to FIG. 6, the body portion 118 may be a tube-like structure that constitutes a substantial segment of the dispensing body 104. The cross-section of the body portion 118 may be oval-shaped, although other shapes are possible depending on the structure of the frame portion. The e-vapor apparatus may be held by the body portion 118. Accordingly, the body portion 118 may be formed of (or covered with) a material that provides enhanced gripping and/or texture appeal to the fingers.

Figure 7:
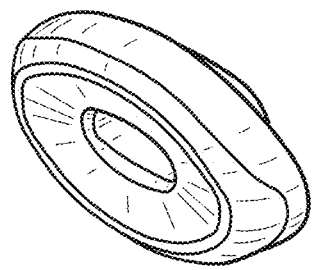
FIG. 7 is a perspective view of the end piece of FIG. 2.

FIG. 7 is a perspective view of the end piece of FIG. 2. Referring to FIG. 7, the end piece 120 is configured to be inserted in the distal end of the body portion 118. The shape of the end piece 120 may correspond to the shape of the distal end of the body portion 118 so as to provide a relatively smooth and continuous transition between the two surfaces.

Figure 8:
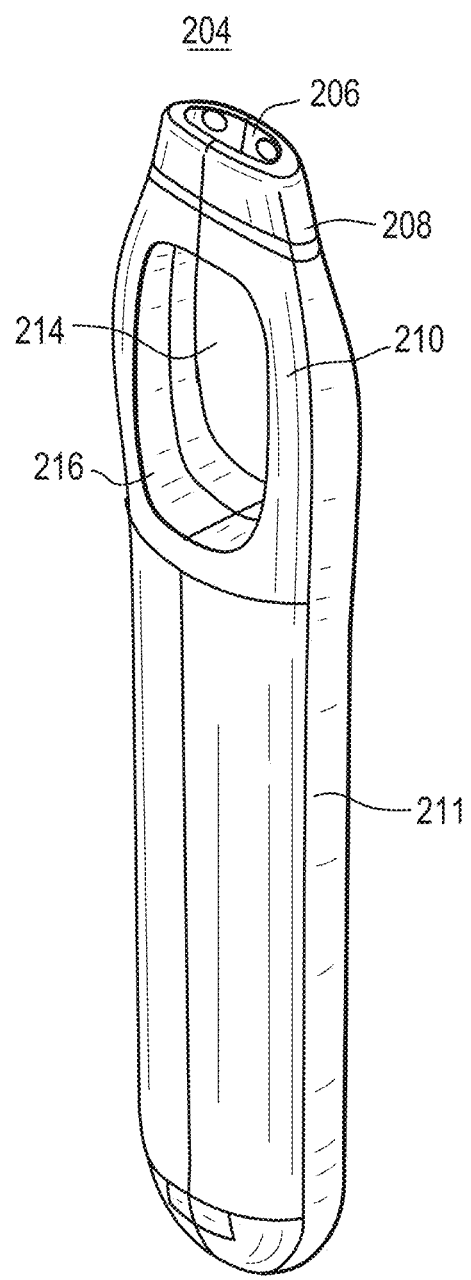
FIG. 8 is a perspective view of another dispensing body of an e-vapor apparatus according to an example embodiment.

FIG. 8 is a perspective view of another dispensing body of an e-vapor apparatus according to an example embodiment. Referring to FIG. 8, the dispensing body 204 includes a side wall 216 defining a through-hole 214 that is configured to receive a pod assembly. A substantial portion of the framework of the dispensing body 204 is provided by the first frame 210, the frame trim 211, and the second frame 212 (e.g., FIG. 9). A vapor passage 206 and a first mouthpiece 208 are provided at a proximal portion of the dispensing body 204.

Figure 9:
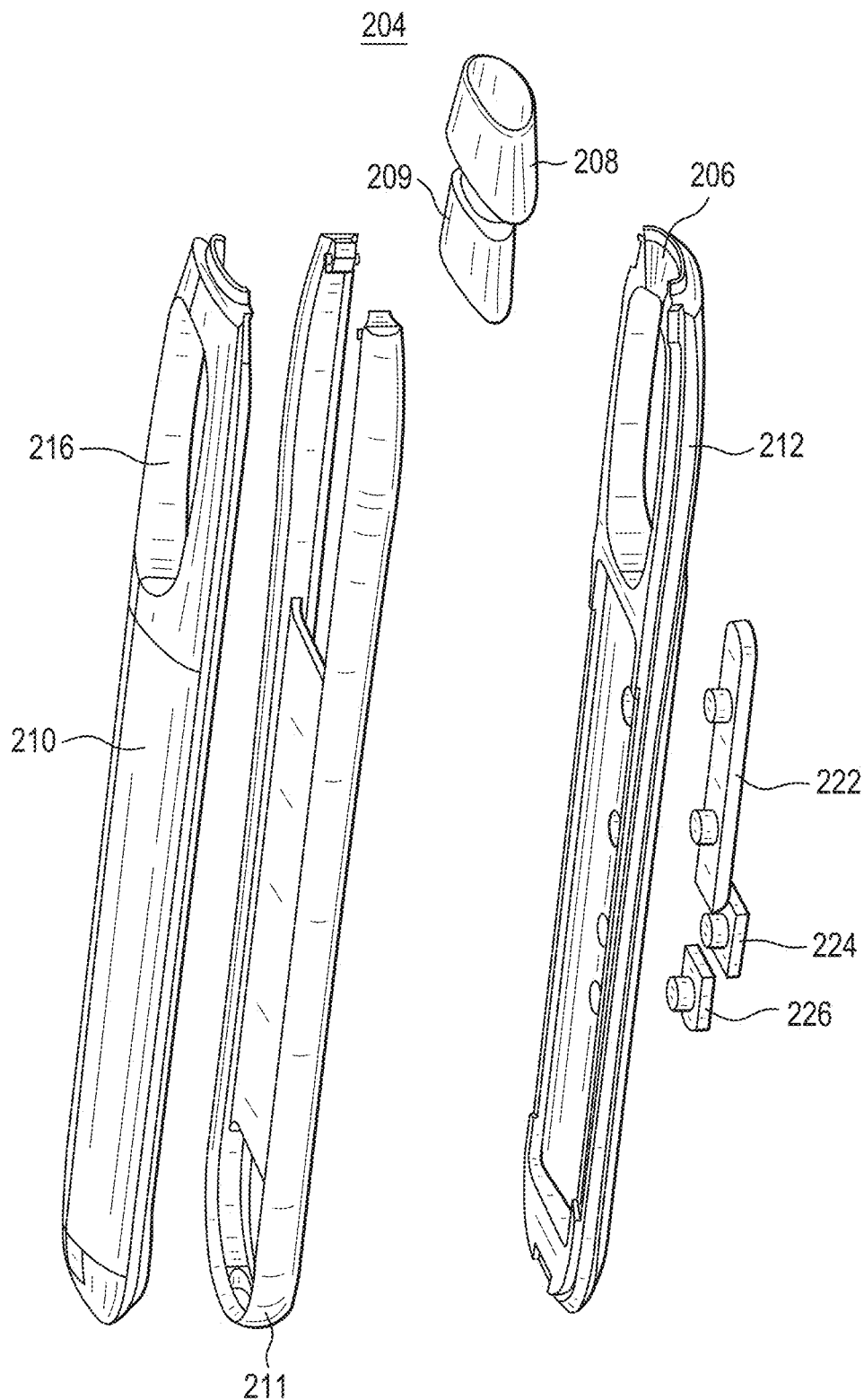
FIG. 9 is an exploded view of the dispensing body of FIG. 8.

FIG. 9 is an exploded view of the dispensing body of FIG. 8. Referring to FIG. 9, the frame trim 211 is sandwiched between the first frame 210 and the second frame 212. However, it should be understood that it is possible to modify and structure the first frame 210 and the second frame 212 such that the frame trim 211 is not needed. The vapor passage 206 may be defined by both the proximal ends of the first frame 210 and the second frame 212 as well as the second mouthpiece 209. As a result, the vapor passage 206 extends from the side wall 216 to the outlet end of the second mouthpiece 209. The first mouthpiece 208 is configured to slip onto the second mouthpiece 209. In an example embodiment, the first mouthpiece 208 may be structured to be removable, while the second mouthpiece 209 may be structured to be permanent. Alternatively, the first mouthpiece 208 may be integrated with the second mouthpiece 209 to form a single structure that is removable.

A first button 222, a second button 224, and a third button 226 may be provided on the second frame 212 of the dispensing body 204. In an example embodiment, the first button 222 may be a display (e.g., battery level indicator), the second button 224 may control an amount of pre-vapor formulation available to the heater, and the third button 226 may be the power button. However, it should be understood that example embodiments are not limited thereto. For example, the third button 226 may be a capacitive slider. Notably, the buttons can have different implementations depending on the desired functionalities. Accordingly, a different number of buttons (and/or of different shapes) may be provided in the same proximity or at a different location on the e-vapor apparatus. Furthermore, the features and considerations in connection with the dispensing body 104 that are also applicable to the dispensing body 204 may be as discussed supra in connection with the dispensing body 104.

Figure 10:
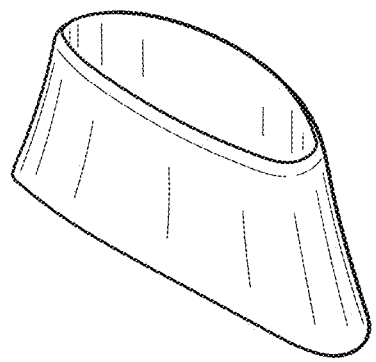
FIG. 10 is a perspective view of the first mouthpiece of FIG. 9.

FIG. 10 is a perspective view of the first mouthpiece of FIG. 9. Referring to FIG. 10, the first mouthpiece 208 is configured to fit over the second mouthpiece 209. Thus, the inner surface of the first mouthpiece 208 may correspond to an outer surface of the second mouthpiece 209.

Figure 11:
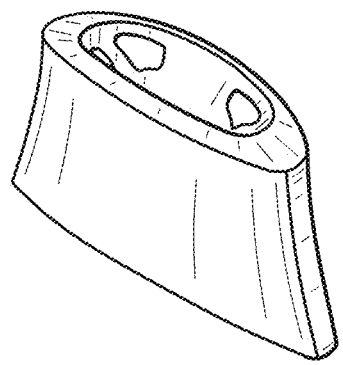
FIG. 11 is a perspective view of the second mouthpiece of FIG. 9.

FIG. 11 is a perspective view of the second mouthpiece of FIG. 9. Referring to FIG. 11, the second mouthpiece 209 defines a vapor passage 206 therein. The second mouthpiece 209 may resemble the combined proximal ends of the first frame 110 and the second frame 112 that define the vapor passage 106 of the dispensing body 104.

Figure 12:
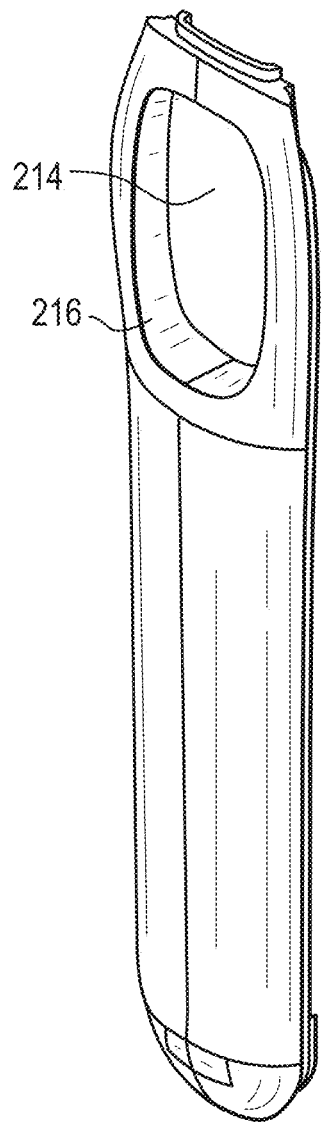
FIG. 12 is a perspective view of the first frame of FIG. 9.

FIG. 12 is a perspective view of the first frame of FIG. 9. Referring to FIG. 12, the first frame 210 includes a side wall 216 that defines a through-hole 214. The top end of the first frame 210 may include a connection structure that facilitates the connection of at least the second mouthpiece 209 thereto.

Figure 13:
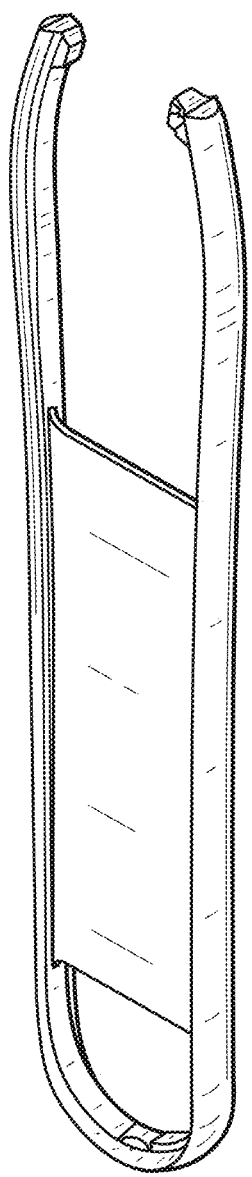
FIG. 13 is a perspective view of the frame trim of FIG. 9.

FIG. 13 is a perspective view of the frame trim of FIG. 9. Referring to FIG. 13, the frame trim 211 may be in the form of a curved strip that is supported by a central plate. When arranged between the first frame 210 and the second frame 212, the frame trim 211 forms a side surface of the dispensing body 204, although example embodiments are not limited thereto.

Figure 14:
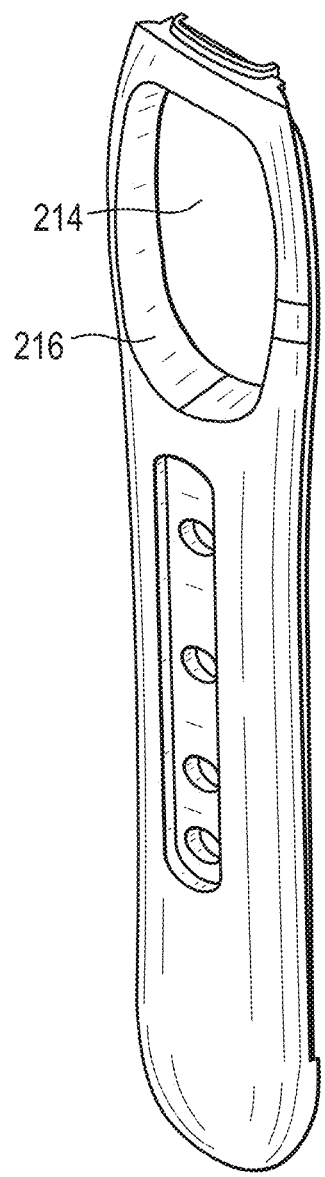
FIG. 14 is a perspective view of the second frame of FIG. 9.

FIG. 14 is a perspective view of the second frame of FIG. 9. Referring to FIG. 14, the second frame 212 includes a side wall 216 that defines a through-hole 214. The top end of the second frame 212 may include a connection structure that facilitates the connection of at least the second mouthpiece 209 thereto. In addition, the surface of the second frame 212 may be provided with a pattern or textured appearance. Such patterning and texturing may be aesthetic (e.g., visually appealing) and/or functional (e.g., enhanced grip) in nature. Although not shown, the surface of the first frame 210 may be similarly provided.

Figure 15:
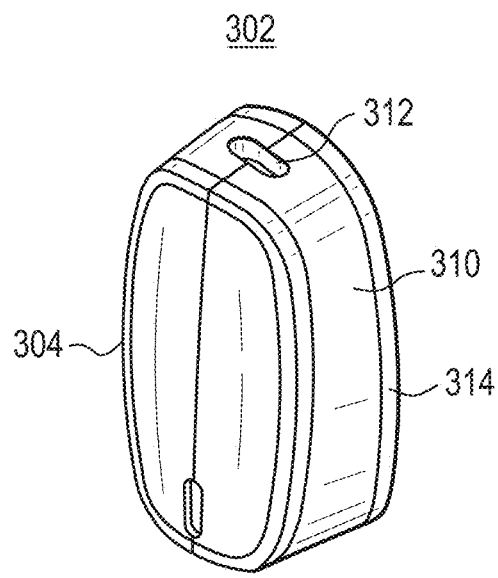
FIG. 15 is a perspective view of a pod assembly of an e-vapor apparatus according to an example embodiment.

FIG. 15 is a perspective view of a pod assembly of an e-vapor apparatus according to an example embodiment. Referring to FIG. 15, the pod assembly 302 includes a pod trim 310 that is arranged between a first cap 304 and a second cap 314. The first cap 304 may be regarded as a front cap, and the second cap 314 may be regarded as a rear cap (or vice versa). The first cap 304 and the second cap 314 may be formed of a transparent material to permit a viewing of the contents (e.g., pre-vapor formulation) in the pod assembly 302. The pod trim 310 defines a channel outlet 312 for the release of vapor generated within the pod assembly 302.

The pod assembly 302 is a self-contained article that can be sealed with a protective film that wraps around the pod trim 310. Additionally, because of the closed system nature of the pod assembly 302, the risk of tampering and contamination can be reduced. Also, the chance of unwanted physical exposure to the pre-vapor formulation within the pod assembly 302 (e.g., via a leak) can be reduced. Furthermore, the pod assembly 302 can be structured so as to prevent refilling.

Figure 16:
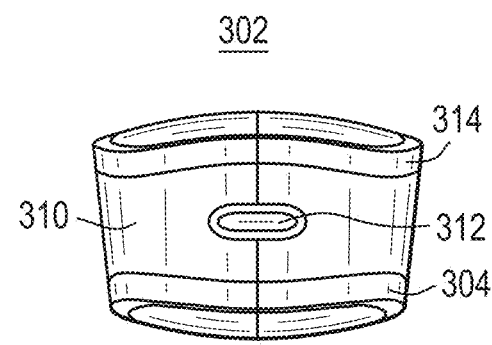
FIG. 16 is a top view of the pod assembly of FIG. 15.

FIG. 16 is a top view of the pod assembly of FIG. 15. Referring to FIG. 16, the second cap 314 is wider than the first cap 304. As a result, the pod trim 310 may slant outwards from the first cap 304 to the second cap 314. However, it should be understood that other configurations are possible depending on the design of the pod assembly 302.

Figure 17:
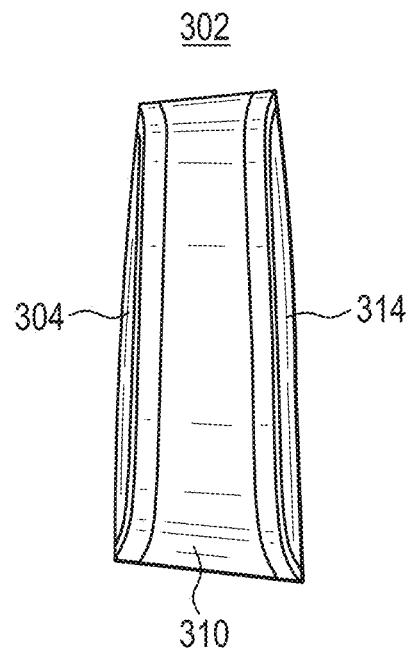
FIG. 17 is a side view of the pod assembly of FIG. 15.

FIG. 17 is a side view of the pod assembly of FIG. 15. Referring to FIG. 17, the second cap 314 is longer than the first cap 304. As a result, the pod trim 310 may slant outwards from the first cap 304 to the second cap 314. As a result, the pod assembly 302 may be inserted in a dispensing body such that the side corresponding to the first cap 304 is received in the through-hole first. In an example embodiment, the pod assembly 302 may be inserted in the through-hole 114 of the dispensing body 104 and/or the through-hole 214 of the dispensing body 204.

Figure 18:
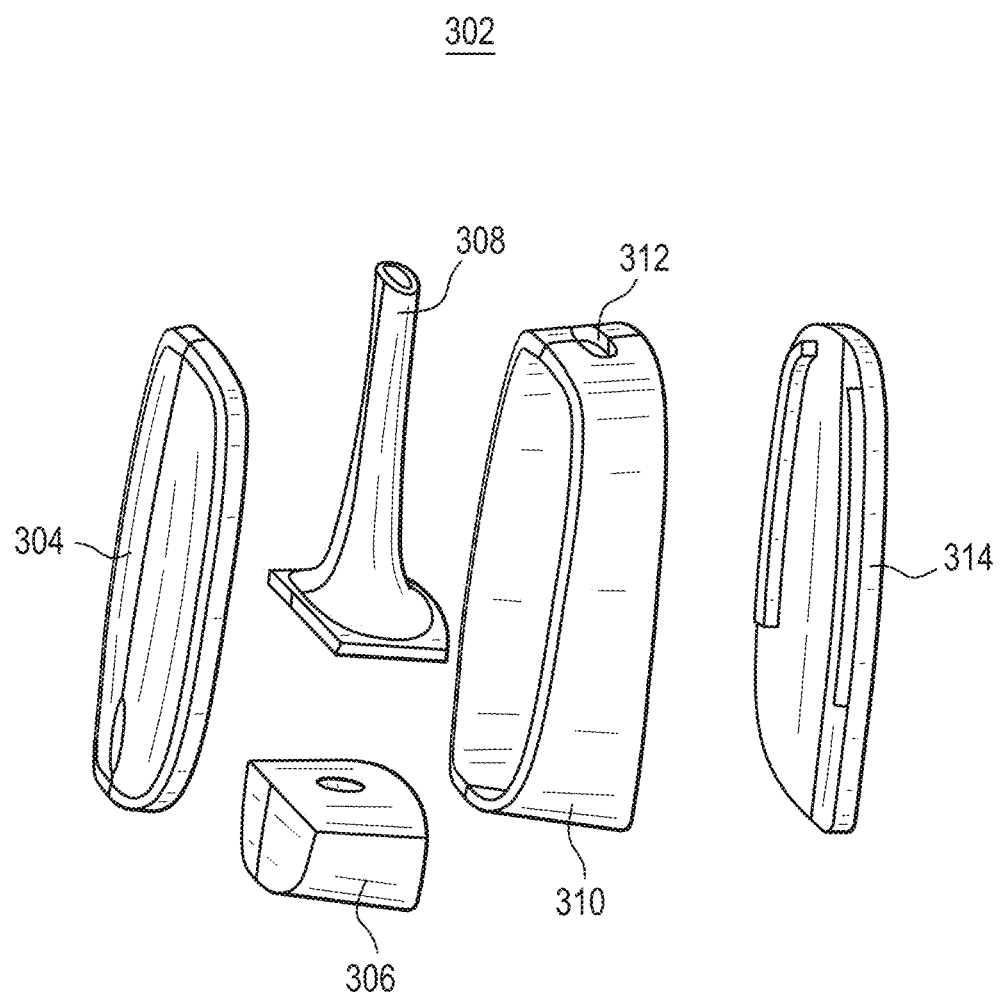
FIG. 18 is an exploded view of the pod assembly of FIG. 15.

FIG. 18 is an exploded view of the pod assembly of FIG. 15. Referring to FIG. 18, the internal space of the pod assembly 302 may be divided into a plurality of compartments by virtue of the elements therein. For instance, the tapered outlet of the vapor channel 308 may be aligned with the channel outlet 312, and the space bounded by the first cap 304, the vapor channel 308, the pod trim 310, and the second cap 314 may be regarded as the pre-vapor formulation compartment. Additionally, the bounded space under the vapor channel 308 may be regarded as the device compartment. For instance, the device compartment may include the vaporizer 306. One benefit of including the vaporizer 306 in the pod assembly 302 is that the vaporizer 306 will only be used for the amount of pre-vapor formulation contained within the pre-vapor formulation compartment and, thus, will not be overused.

Figure 19:
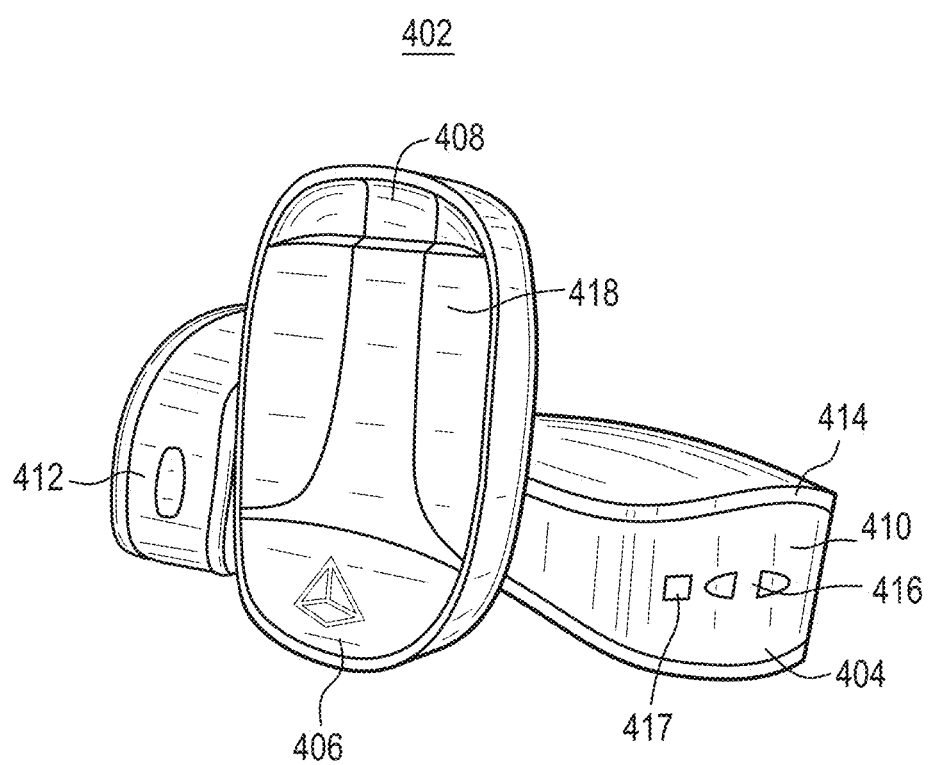
FIG. 19 a perspective view of several pod assemblies according to an example embodiment.

FIG. 19 a perspective view of several pod assemblies according to an example embodiment. Referring to FIG. 19, each of the pod assemblies 402 includes a pod trim 410 arranged between a first cap 404 and a second cap 414. The vapor channel 408 is aligned with the channel outlet 412 and arranged above the vaporizer 406. The pod assembly 402 is sealed to hold a pre-vapor formulation 418 therein and to preclude tampering therewith. As shown in the example embodiment of FIG. 19, the pre-vapor formulation 418 fills to near a top of the pod assembly 402.

The pre-vapor formulation compartment of the pod assembly 402 is configured to hold the pre-vapor formulation 418, and the device compartment includes the vaporizer 406. The pod assembly 402 includes battery contacts 416 and a data connection 417 connected to a cryptographic coprocessor with non-volatile memory (CC-NVM) within the pod assembly 402. For example, the CC-NVM may be connected to a portion of the pod assembly 402 separate from the vaporizer 406 and pre-vapor formulation 418. In one example embodiment, the CC-NVM is attached to an internal surface of the trim 410. In another example embodiment, the CC-NVM is connected to a printed circuit board (PCB) in the pod assembly that is separate from the vaporizer 406 and pre-vapor formulation 418. Thus, the pod assembly 402 may be considered to have at least three sections, one with the pre-vapor, one where the vaporizer resides and one containing the connector bits and the CC-NVM.

The term CC-NVM may refer to a hardware module(s) including a processor for encryption and related processing.

In further detail, the pod assembly 402 for an e-vapor apparatus may include a pre-vapor formulation compartment configured to hold a pre-vapor formulation 418 therein. A device compartment is in fluidic communication with the pre-vapor formulation compartment. The device compartment includes a vaporizer 406. A vapor channel 408 extends from the device compartment and traverses the pre-vapor formulation compartment.

The pod assembly 402 is configured for insertion into a dispensing body. As a result, the dimensions of the pod assembly 402 may correspond to the dimensions of the through-hole (e.g., 114) of the dispensing body (e.g., 104). The vapor channel 408 may be between the mouthpiece (e.g., 108) and the device compartment when the pod assembly 402 is inserted into the through-hole of the dispensing body.

An attachment structure (e.g., male/female member arrangement, magnetic arrangement) may be provided on at least one of the side walls (e.g., 116) of the through-hole (e.g., 114) and a side surface of the pod assembly 402. The attachment structure may be configured to engage and hold the pod assembly 402 upon insertion into the through-hole of the dispensing body. In addition, the channel outlet 412 may be utilized to secure the pod assembly 402 within the through-hole of the dispensing body. For instance, the dispensing body may be provided with a retractable vapor connector that is configured to insert into the channel outlet 412 so as to secure the pod assembly 402 while also supplementing the vapor path from the channel outlet 412 to the vapor passage (e.g., 106) of the dispensing body (e.g., 104). The vapor connector may also be a rounded structure and/or spring-loaded to facilitate its retraction (e.g., via spring compression) and protraction (e.g., via spring decompression).

In an example embodiment, the pre-vapor formulation compartment of the pod assembly 402 may surround the vapor channel 408. For instance, the vapor channel 408 may pass through a center of the pre-vapor formulation compartment, although example embodiments are not limited thereto.

Alternatively, instead of the vapor channel 408 shown in FIG. 19, a vapor channel may be in a form of a pathway that is arranged along at least one sidewall of the pre-vapor formulation compartment. For example, a vapor channel may be provided in a form of a pathway that spans between the first cap 404 and the second cap 414 while extending along one or both sides of an inner surface of the pod trim 410. As a result, the pathway may have a thin, rectangular cross-section, although example embodiments are not limited thereto. When the pathway is arranged along two sidewalls of the pre-vapor formulation compartment (e.g., both inner sidewalls of the pod trim 410), the pathway along each sidewall may be configured to converge at a position (e.g., channel outlet 412) that is aligned with the vapor passage (e.g., 106) of the dispensing body (e.g., 104) when the pod assembly 402 is received in the through-hole 114.

In another instance, the vapor channel may be in a form of a conduit that is arranged in at least one corner of the pre-vapor formulation compartment. Such a corner may be at the interface of the first cap 404 and/or the second cap 414 with the inner surface of the pod trim 410. As a result, the conduit may have a triangular cross-section, although example embodiments are not limited thereto. When the conduit is arranged in at least two corners (e.g., front corners, rear corners, diagonal corners, side corners) of the pre-vapor formulation compartment, the conduit in each corner may be configured to converge at a position (e.g., channel outlet 412) that is aligned with the vapor passage (e.g., 106) of the dispensing body (e.g., 104) when the pod assembly 402 is received in the through-hole 114.

The pre-vapor formulation compartment and the device compartment may be at opposite ends of the pod assembly 402. The device compartment may include a memory device. The memory device may be coded with an electronic identity to permit at least one of an authentication of the pod assembly 402 and a pairing of operating parameters specific to a type of the pod assembly 402 when the pod assembly 402 is inserted into the through-hole of the dispensing body (e.g., smart calibration). The electronic identity may help prevent counterfeiting. The operating parameters may help improve a vaping experience. In an example embodiment, the level of pre-vapor formulation in the pod assembly 402 may be tracked. Additionally, the activation of the pod assembly 402 may be restricted once its intended usage life has been exceeded. Thus, the pod assembly 402 (and 302) may be regarded as a smart pod.

A side surface of the pod assembly 402 includes at least one electrical contact 416 (e.g., two or three electrical contacts) and at least one electrical contact 417 (data connection) for data. The CC-NVM package is connected to the electrical contact 416 and one of the contacts 416. The dispensing body may be configured to perform at least one of supply power to and communicate with the pod assembly 402 via the at least one electrical contact 416. The at least one electrical contact 416 may be provided at an end of the pod assembly 402 corresponding to the device compartment. Because of its smart capability, the pod assembly 402 may communicate with dispensing body and/or another electronic device (e.g., smart phone). As a result, usage patterns and other information (e.g., puff size, flavor intensity, throat feel, puff count) may be generated, stored, transferred, and/or displayed. The smart capability, connecting features, and other related aspects of the pod assembly, dispensing body, and overall e-vapor apparatus are additionally discussed in U.S. Application No. 62/151,148 filed on Apr. 22, 2015, entitled POD ASSEMBLY, DISPENSING BODY, AND E-VAPOR APPARATUS INCLUDING THE SAME, and U.S. Application No. 62/151,248 filed on Apr. 22, 2015, entitled E-VAPOR DEVICES INCLUDING PRE-SEALED CARTRIDGES, the entire contents of each of which are incorporated herein by reference.

Figure 20:
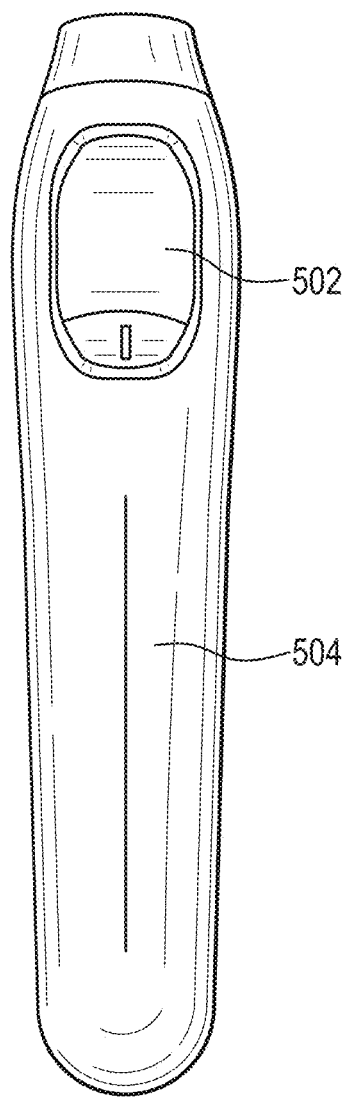
FIG. 20 is a view of an e-vapor apparatus with a pod assembly inserted in a dispensing body according to an example embodiment.

FIG. 20 is a view of an e-vapor apparatus with a pod assembly inserted in a dispensing body according to an example embodiment. Referring to FIG. 20, an e-vapor apparatus 500 includes a pod assembly 502 (e.g., smart pod) that is inserted within a dispensing body 504. The pod assembly 502 may be as previously described in connection with the pod assembly 302 and the pod assembly 402. As a result, the pod assembly 502 may be a hassle-free and leak-free element that can be replaced with relative ease when the pre-vapor formulation therein runs low/out or when another pod is desired.

Figure 21:
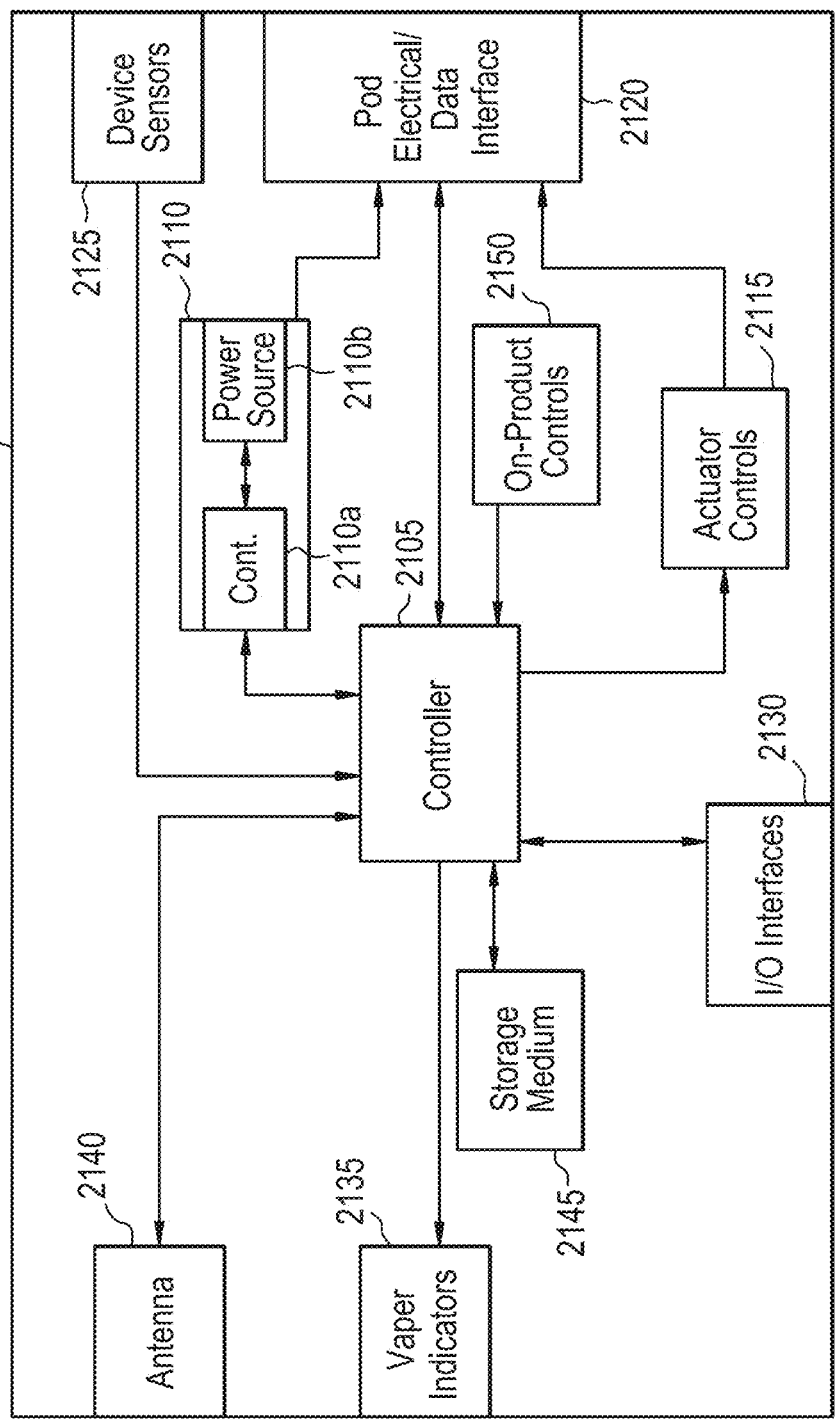
FIG. 21 illustrates a device system diagram of a dispensing body according to an example embodiment.

FIG. 21 illustrates a device system of a dispensing body according to an example embodiment. A device system 2100 may be the system within the dispensing body 104 and the dispensing body 204.

The device system 2100 includes a controller 2105, a power supply 2110, actuator controls 2115, a pod electrical/data interface 2120, device sensors 2125, input/output (I/O) interfaces 2130, vaper indicators 2135, at least one antenna 2140 and a storage medium 2145. The device system 2100 is not limited to the features shown in FIG. 21. For example, the device system 2100 may include additional elements. However, for the sake of brevity, the additional elements are not described. In other example embodiments, the device system 2100 may not include an antenna.

The controller 2105 may be hardware, firmware, hardware executing software or any combination thereof. When the controller 2105 is hardware, such existing hardware may include one or more Central Processing Units (CPUs), digital signal processors (DSPs), application-specific-integrated-circuits (ASICs), field programmable gate arrays (FPGAs) computers or the like configured as special purpose machines to perform the functions of the controller 2105. As stated above, CPUs, DSPs, ASICs and FPGAs may generally be referred to as processing devices.

In the event where the controller 2105 is a processor executing software, the controller 2105 is configured as a special purpose machine to execute the software, stored in the storage medium 2145, to perform the functions of the controller 2105.

As disclosed herein, the term "storage medium", "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Referring to FIG. 21, the controller 2105 communicates with the power supply 2110, the actuator control 2115, the pod electrical/data interface 2120, the device sensors 2125, the input/output (I/O) interfaces 2130, the vaper indicators 2135, the at least one antenna 2140.

The controller 2105 communicates with the CC-NVM in the pod through the pod electrical/data interface 2120. More specifically, the controller 2105 may utilize encryption to authenticate the pod. As will be described, the controller 2105 communicates with the CC-NVM package to authenticate the pod. More specifically, the non-volatile memory is encoded during manufacture with product and other information for authentication.

The memory device may be coded with an electronic identity to permit at least one of an authentication of the pod and a pairing of operating parameters specific to a type of the pod (or physical construction, such as a heating engine type) when the pod assembly 402 is inserted into the through-hole of the dispensing body. In addition to authenticating based on an electronic identity of the pod, the controller 2105 may authorize use of the pod based on an expiration date of the stored pre-vapor formulation and/or heater information encoded into the non-volatile memory of the CC-NVM. If the controller determines that the expiration date encoded into the non-volatile memory has passed, the controller may not authorize use of the pod and disable the e-vaping device.

The controller 2105 (or storage medium 2145) stores key material and proprietary algorithm software for the encryption. For example, encryption algorithms rely on the use of random numbers. The security of these algorithms depends on how truly random these numbers are. These numbers are usually pre-generated and coded into the processor or memory devices. Example embodiments may increase the randomness of the numbers used for the encryption by using the puffing parameters e.g., puff durations, intervals between puffs, or combinations of them, to generate numbers that are more random and more varying from individual to individual than pre-generated random numbers. All communications between the controller 2105 and the pod may be encrypted.

Moreover, the pod can be used to as a general pay-load carrier for other information such as software patches for the e-vaping device. Since encryption is used in all the communications between the pod and the controller 2105, such information is more secure and the e-vaping device is less prone to being installed with malwares or viruses. Use of the CC-NVM as an information carrier such as data and software updates allows the e-vaping device to be updated with software without it being connected to the Internet and for an adult vaper to go through a downloading process as with most other consumer electronics devices requiring periodic software updates.

The controller 2105 may also include a cryptographic accelerator to allow resources of the controller 2105 to perform functions other than the encoding and decoding involved with the authentication. The controller 2105 may also include other security features such as preventing unauthorized use of communication channels and preventing unauthorized access to data if a pod or adult vaper is not authenticated.

In addition to a cryptographic accelerator, the controller 2105 may include other hardware accelerators. For example, the controller 2105 may include a floating point unit (FPU), a separate DSP core, digital filters and Fast Fourier Transform (FFT) modules.

The controller 2105 is configured to operate a real time operating system (RTOS), control the system 2100 and may be updated through communicating with the CC-NVM or when the system 2100 is connected with other devices (e.g., a smart phone) through the I/O interfaces 2130 and/or the antenna 2140. The I/O interfaces 2130 and the antenna 2140 allow the system 2100 to connect to various external devices such as smart phones, tablets, and PCs. For example, the I/O interfaces 2130 may include a micro-USB connector. The micro-USB connector may be used by the system 2100 to charge the power source 2110b.

The controller 2105 may include on-board RAM and flash memory to store and execute code including analytics, diagnostics and software upgrades. As an alternative, the storage medium 2145 may store the code. Additionally, in another example embodiment, the storage medium 2145 may be on-board the controller 2105.

The controller 2105 may further include on-board clock, reset and power management modules to reduce an area covered by a PCB in the dispensing body.

The device sensors 2125 may include a number of sensor transducers that provide measurement information to the controller 2105. The device sensors 2125 may include a power supply temperature sensor, an external pod temperature sensor, a current sensor for the heater, power supply current sensor, air flow sensor and an accelerometer to monitor movement and orientation. The power supply temperature sensor and external pod temperature sensor may be a thermistor or thermocouple and the current sensor for the heater and power supply current sensor may be a resistive based sensor or another type of sensor configured to measure current. The air flow sensor may be a microelectromechanical system (MEMS) flow sensor or another type of sensor configured to measure air flow such as a hot-wire anemometer.

The data generated from the number of sensor transducers may be sampled at a sample rate appropriate to the parameter being measured using a discrete, multi-channel analog-to-digital converter (ADC).

The controller 2105 may adapt heater profiles for a pre-vapor formulation and other profiles based on the measurement information received from the controller 2105. For the sake of convenience, these are generally referred to as vaping or vapor profiles.

The heater profile identifies the power profile to be supplied to the heater during the few seconds when puffing takes place. For example, a heater profile can be: deliver maximum power to the heater when a puff is initiated, but then after a second or so immediately reduce the power to half way or a quarter way.

The modulation of electrical power is usually implemented using pulse width modulation—instead of flipping an on/off switch where the power is either full on or off.

In addition, a heater profile can also be modified based on a negative pressure applied on the e-vaping device. The use of the MEMS flow sensor allows puff strength to be measured and used as feedback to the controller 2105 to adjust the power delivered to the heater of the pod, which may be referred to as heating or energy delivery.

When the controller 2105 recognizes the pod currently installed (e.g., via SKU), the controller 2105 matches an associated heating profile that is designed for that particular pod. The controller 2105 and the storage medium 2145 will store data and algorithms that allow the generation of heating profiles for all SKUs. In another example embodiment, the controller 2105 may read the heating profile from the pod. The adult vapers may also adjust heating profiles to suit their preferences.

As shown in FIG. 21, the controller 2105 sends data to and receives data from the power supply 2110. The power supply 2110 includes a power source 2110b and a power controller 2110a to manage the power output by the power source 2110b.

The power source 2110b may be a Lithium-ion battery or one of its variants, for example a Lithium-ion polymer battery. Alternatively, the power source power source 2110b may be a Nickel-metal hydride battery, a Nickel cadmium battery, a Lithium-manganese battery, a Lithium-cobalt battery or a fuel cell. Alternatively, the power source 2110b may be rechargeable and include circuitry allowing the battery to be chargeable by an external charging device. In that case, the circuitry, when charged, provides power for a desired (or alternatively a pre-determined) number of puffs, after which the circuitry must be re-connected to an external charging device.

The power controller 2110a provides commands to the power source 2110b based on instructions from the controller 2105. For example, the power supply 2110 may receive a command from the controller 2105 to provide power to the pod (through the electrical/data interface 2120) when the pod is authenticated and the adult vaper activates the system 2100 (e.g., by activating a switch such as a toggle button, capacitive sensor, IR sensor). When the pod is not authenticated, the controller 2105 may either send no command to the power supply 2110 or send an instruction to the power supply 2110 to not provide power. In another example embodiment, the controller 2105 may disable all operations of the system 2100 if the pod is not authenticated.

In addition to supplying power to the pod, the power supply 2110 also supplies power to the controller 2105. Moreover, the power controller 2110a may provide feedback to the controller 2105 indicating performance of the power source 2110b.

The controller 2105 sends data to and receives data from the at least one antenna 2140. The at least one antenna 2140 may include a Near Field Communication (NFC) modem and a Bluetooth Low Energy (LE) modem and/or other modems for other wireless technologies (e.g., Wi-Fi). In an example embodiment, the communications stacks are in the modems, but the modems are controlled by the controller 2105. The Bluetooth LE modem is used for data and control communications with an application on an external device (e.g., smart phone). The NFC modem may be used for pairing of the e-vaping device to the application and retrieval of diagnostic information. Moreover, the Bluetooth LE modem may be used to provide location information (for an adult vaper to find the e-vaping device) or authentication during a purchase.

As described above, the system 2100 may generate and adjust various profiles for vaping. The controller 2105 uses the power supply 2110 and the actuator controls 2115 to regulate the profile for the adult vaper.

The actuator controls 2115 include passive and active actuators to regulate a desired vapor profile. For example, the dispensing body may include an inlet channel within a mouthpiece. The actuator controls 2115 may control the inlet channel based on commands from the controller 2105 associated with the desired vapor profile.

Moreover, the actuator controls 2115 are used to energize the heater in conjunction with the power supply 2110. More specifically, the actuator controls 2115 are configured to generate a drive waveform associated with the desired vaping profile. As described above, each possible profile is associated with a drive waveform. Upon receiving a command from the controller 2105 indicating the desired vaping profile, the actuator controls 2115 may produce the associated modulating waveform for the power supply 2110.

The controller 2105 supplies information to the vaper indicators 2135 to indicate statuses and occurring operations to the adult vaper. The vaper indicators 2135 include a power indicator (e.g., LED) that may be activated when the controller 2105 senses a button pressed by the adult vaper. The vaper indicators 2135 may also include a vibrator, speaker, an indicator for current state of an adult vaper-controlled vaping parameter (e.g., vapor volume) and other feedback mechanisms.

Furthermore, the system 2100 may include a number of on-product controls 2150 that provide commands from an adult vaper to the controller 2105. The on-product controls 2150 include an on-off button which may be a toggle button, capacitive sensor or IR sensor, for example. The on-product controls 2150 may further include a vaping control button (if the adult vaper desires to override the buttonless vaping feature to energize the heater), a hard reset button, a touch based slider control (for controlling setting of a vaping parameter such as puff volume), a vaping control button to activate the slider control and a mechanical adjustment for an air inlet.

Once a pod is authenticated, the controller 2105 operates the power supply 2110, the actuator controls 2115, vaper indicators 2135 and antenna 2140 in accordance with the adult vaper using the e-vaping device and the information stored by the CC-NVM on the pod. Moreover, the controller 2105 may include logging functions and be able to implement algorithms to calibrate the e-vaping device. The logging functions are executed by the controller 2105 to record usage data as well any unexpected events or faults. The recorded usage data may be used for diagnostics and analytics. The controller 2105 may calibrate the e-vaping device using buttonless vaping (i.e., vaping without pressing a button such as generating a vapor when a negative pressure is applied on the mouthpiece), an adult vaper configuration and the stored information on the CC-NVM including puff sensing, pre-vapor formulation level and pre-vapor formulation composition. For example, the controller 2105 may command the power supply 2110 to supply power to the heater in the pod based on a vaping profile associated with the pre-vapor formulation composition in the pod. Alternatively, a vaping profile may be encoded in the CC-NVM and utilized by the controller 2105.

Figure 22:
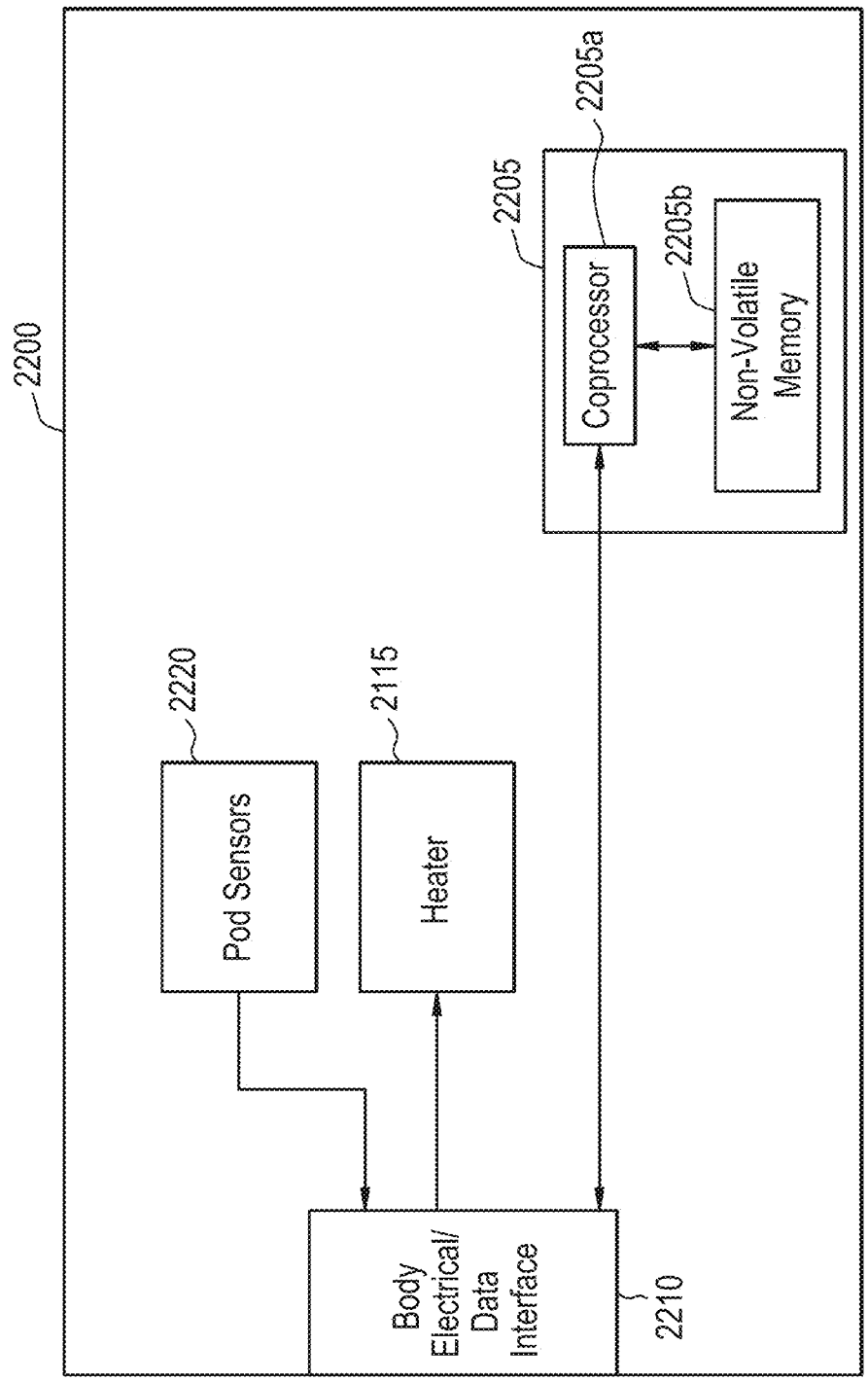
FIG. 22 illustrates a pod system diagram of a dispensing body according to an example embodiment.

FIG. 22 illustrates a pod system diagram of a dispensing body according to an example embodiment. A pod system 2200 may be within the pod assembly 502, the pod assembly 302 and the pod assembly 402.

As shown in FIG. 22, the pod system 2200 includes a CC-NVM 2205, a body electrical/data interface 2210, a heater 2215 and pod sensors 2220. The pod system 2200 communicates with the device system 2100 through the body electrical/data interface 2210 and the pod electrical/data interface 2120. The body electrical/data interface 2210 may correspond to the battery contacts 416 and data connection 417 connected within the pod assembly 402, shown in FIG. 19, for example. Thus, the CC-NVM 2205 is coupled to the data connection 417 and the battery contacts 416.

The CC-NVM 2205 includes a cryptographic coprocessor 2205a and a non-volatile memory 2205b. The controller 2105 may access the information stored on the non-volatile memory 2205b for the purposes of authentication and operating the pod by communicating with the cryptographic coprocessor 2205a. In another example embodiment, the pod may not have a crytopgraphic coprocessor. When no cryptographic coprocessor exists, the controller 2105 may read data from the non-volatile memory 2205b without use of the cryptographic coprocessor to control/define the heating profile.

The non-volatile memory 2205b may be coded with an electronic identity to permit at least one of an authentication of the pod and a pairing of operating parameters specific to a type of the pod when the pod assembly is inserted into the through-hole of the dispensing body. In addition to authenticating based on an electronic identity of the pod, the controller 2105 may authorize use of the pod based on an expiration date of the stored pre-vapor formulation and/or heater encoded into the non-volatile memory 2205b of the CC-NVM. If the controller determines that the expiration date encoded into the non-volatile memory non-volatile memory 2205b has passed, the controller may not authorize use of the pod and disable the e-vaping device.

Moreover, the non-volatile memory 2205b may store information such as a stock keeping unit (SKU) of the pre-vapor formulation in the pre-vapor formulation compartment (including pre-vapor formulation composition), software patches for the system 2100, product usage information such as puff count, puff duration, and pre-vapor formulation level. The non-volatile memory 2205b may store operating parameters specific to the type of the pod and the pre-vapor formulation composition. For example, the non-volatile memory 2205b may store the electrical and mechanical design of the pod for use by the controller 2105 to determine commands corresponding to a desired vaping profile.

The pre-vapor formulation level in the pod may be determined in one of two ways, for example. In one example embodiment, one of the pod sensors 2220 directly measures the pre-vapor formulation level in the pod.

In another example embodiment, the non-volatile memory 2205b stores the puff count from the pod and the controller 2105 uses the puff count as a proxy to the amount of pre-vapor formulation vaporized.

The controller 2105 and/or the storage medium 2145 may store pre-vapor formulation calibration data that identifies an operating point for the pre-vapor formulation composition. The pre-vapor formulation calibration data include data describing how flow rate changes with a remaining pre-vapor formulation level or how volatility changes with an age of the pre-vapor formulation and may be used for calibration by the controller 2105. The pre-vapor formulation calibration data may be stored by the controller 2105 and/or the storage medium 2145 in a table format. The pre-vapor formulation calibration data allows the controller 2105 to equate the puff count to the amount of pre-vapor formulation vaporized.

The controller 2105 writes the pre-vapor formulation level and puff count back to the non-volatile memory 2205b in the pod so if the pod is removed from the dispensing body and later on re-installed, an accurate pre-vapor formulation level of the pod will still be known by the controller 2105.

The operating parameters (e.g., power supply, power duration, air channel control) are referred to as a vaping profile. Moreover, the non-volatile memory 2205b may record information communicated by the controller 2105. The non-volatile memory 2205b may retain the recorded information even when the dispensing body becomes disconnected from the pod.

In an example embodiment, the non-volatile memory 2205b may be a programmable read only memory.

The heater 2215 is actuated by the controller 2105 and transfers heat to at least a portion of the pre-vapor formulation in accordance with the commanded profile (volume, temperature (based on power profile) and flavor) from the controller 2105.

The heater 2215 may be a wire coil surrounding a wick, a mesh, a surface or made out of a ceramic material for example. Examples of suitable electrically resistive materials include titanium, zirconium, tantalum and metals from the platinum group. Examples of suitable metal alloys include stainless steel, nickel-, cobalt-, chromium-, aluminium- titanium- zirconium-, hafnium-, niobium-, molybdenum-, tantalum-, tungsten-, tin-, gallium-, manganese- and iron-containing alloys, and super-alloys based on nickel, iron, cobalt, stainless steel. For example, the heater may be formed of nickel aluminides, a material with a layer of alumina on the surface, iron aluminides and other composite materials, the electrically resistive material may optionally be embedded in, encapsulated or coated with an insulating material or vice-versa, depending on the kinetics of energy transfer and the external physicochemical properties required. In one embodiment, the heater 14 comprises at least one material selected from the group consisting of stainless steel, copper, copper alloys, nickel-chromium alloys, superalloys and combinations thereof. In an embodiment, the heater 2215 is formed of nickel-chromium alloys or iron-chromium alloys. In one embodiment, the heater 2215 can be a ceramic heater having an electrically resistive layer on an outside surface thereof.

In another embodiment, the heater 2215 may be constructed of an iron-aluminide (e.g., FeAl or Fe.sub.3Al), such as those described in commonly owned U.S. Pat. No. 5,595,706 to Sikka et al. filed Dec. 29, 1994, or nickel aluminides (e.g., Ni.sub.3Al), the entire contents of which are hereby incorporated by reference.

The heater 2215 may determine an amount of pre-vapor formulation to heat based on feedback from the pod sensors or the controller 2105. The flow of pre-vapor formulation may be regulated by a micro-capillary or wicking action. Moreover, the controller 2105 may send commands to the heater 2215 to adjust an air inlet to the heater 2215.

The pod sensor 2220 may include a heater temperature sensor, pre-vapor formulation flow rate monitor and air flow monitor. The heater temperature sensor may be a thermistor or thermocouple and the flow rate sensing may be performed by the system 2200 using electrostatic interference or an in-pre-vapor formulation rotator. The air flow sensor may be a microelectromechanical system (MEMS) flow sensor or another type of sensor configured to measure air flow.

The data generated from the pod sensors 2220 may be sampled at a sample rate appropriate to the parameter being measured using a discrete, multi-channel analog-to-digital converter (ADC).

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. An electronic vapor (e-vapor) apparatus comprising:
   a pod including a pre-vapor formulation compartment; and
   a dispensing body including a proximal portion and an opposing distal portion, the proximal portion including a vapor passage and a receiving element, the vapor passage extending from an end surface of the proximal portion to a side wall of the receiving element, the receiving element being between the vapor passage and the distal portion of the dispensing body, the receiving element defining a through-hole of the dispensing body configured to receive the pod such that opposing surfaces of the pod are exposed at opposing openings of the through-hole of the dispensing body, respectively, when the pod is received by the receiving element.

2. The e-vapor apparatus of claim 1, wherein the dispensing body is configured to authenticate the pod based on communicating with a processor in the pod.

3. The e-vapor apparatus of claim 1, wherein the pod includes a memory.

4. The e-vapor apparatus of claim 3, wherein the memory includes an electronic signature to authenticate the pod.

5. The e-vapor apparatus of claim 1, wherein the pod further includes,
   a device compartment; and
   a vapor channel extending from the device compartment and through the pre-vapor formulation compartment, the pre-vapor formulation compartment configured to hold a pre-vapor formulation therein and the device compartment including a processor configured to cause the pod to monitor the pre-vapor formulation compartment and identify the pre-vapor formulation.

6. The e-vapor apparatus of claim 5, further comprising:
   a vaporizer disposed in the pod, in the dispensing body, or in both the pod and the dispensing body, the pre-vapor formulation compartment of the pod configured to be in fluidic communication with the vaporizer during an operation of the e-vapor apparatus such that the pre-vapor formulation from the pre-vapor formulation compartment comes into thermal contact with the vaporizer, the vaporizer configured to vaporize the pre-vapor formulation to produce a vapor that passes through the pod via the vapor channel, wherein the receiving element defines the through-hole of the dispensing body configured to receive the pod such that the vapor channel of the pod is aligned with the vapor passage of the dispensing body so as to facilitate a delivery of the vapor through the vapor passage of the dispensing body, and the processor is configured to cause the pod to communicate operational parameters of the vaporizer to the dispensing body.

7. The e-vapor apparatus of claim 6, wherein the operational parameters correspond to a solution of the pre-vapor formulation.

8. The e-vapor apparatus of claim 6, wherein the operational parameters include battery settings, energy settings, or both battery and energy settings, the battery settings including a power supply value and a power duration value to generate for the pod.

9. The e-vapor apparatus of claim 5, wherein the dispensing body is configured to supply power to the pod, communicate with the pod, or supply power to the pod and communicate with the pod, via at least one electrical contact coupled to the processor.

10. The e-vapor apparatus of claim 9, wherein the at least one electrical contact is on a side of the pod.

11. The e-vapor apparatus of claim 5, wherein the processor is configured to receive usage data from the dispensing body.

12. The e-vapor apparatus of claim 5, wherein the processor is configured to provide liquid usage parameters associated with the pod to the dispensing body.

* * * * *